United States Patent
Tuenge et al.

[19]

[11] Patent Number: 5,954,502
[45] Date of Patent: Sep. 21, 1999

[54] ADJUSTABLE ORTHODONTIC BRACKET ASSEMBLY WITH CONTINUOUS ADJUSTMENT IN ANY ONE OF SIX PLANES OF MOTION

[76] Inventors: Rodney C. Tuenge, 6174 Songbird Cir., Boulder, Colo. 80303-1476; Timothy M. Niebauer, P.O. Box 636, Erie, Colo. 80516; Jess Valentine, 12589 Jay Rd., Erie, Colo. 80516

[21] Appl. No.: 09/128,066

[22] Filed: Aug. 3, 1998

[51] Int. Cl.⁶ ................................... A61C 3/00
[52] U.S. Cl. .................. 433/16; 433/8; 433/18
[58] Field of Search ................... 433/16, 8, 10, 433/9, 11, 12, 13, 14, 15, 18

[56] References Cited

U.S. PATENT DOCUMENTS

| | | | |
|---|---|---|---|
| Re. 34,044 | 8/1992 | Broussard | 433/8 |
| 1,008,663 | 11/1911 | Montague | 433/16 |
| 2,104,192 | 1/1938 | Ford | 32/14 |
| 2,379,011 | 6/1945 | Laskin | 32/14 |
| 3,218,712 | 11/1965 | Wallshein | 433/16 |
| 3,256,602 | 6/1966 | Broussard et al. | 32/14 |
| 3,262,207 | 7/1966 | Kesling | 32/14 |
| 3,461,559 | 8/1969 | Silverman et al. | 433/15 |
| 3,721,005 | 3/1973 | Cohen | 433/16 |
| 4,243,387 | 1/1981 | Prins | 433/16 |
| 4,353,692 | 10/1982 | Karrakussoglu | 433/16 |
| 4,487,581 | 12/1984 | Adler | 433/16 |
| 4,496,317 | 1/1985 | Hulsey | 433/10 |
| 4,533,320 | 8/1985 | Piekarsky | 433/9 |
| 4,597,739 | 7/1986 | Rosenberg | 433/16 |
| 4,669,980 | 6/1987 | Degnan | 433/8 |
| 4,676,746 | 6/1987 | Klapper | 433/16 |

*Primary Examiner*—John J. Wilson
*Assistant Examiner*—Patrick A. Hilsmier

[57] ABSTRACT

An adjustable orthodontic bracket assembly includes a plurality of brackets. Each bracket is attachable to a front face of a tooth such that the bracket is positionable in series relation to one or more other of the brackets. Each bracket is continuously adjustable in at least three planes and, preferably, in six planes of motion without a need to replace any parts thereof. The adjustment of each bracket in one of the planes of motion can be accomplished without affecting the adjustment of the bracket in any of the other planes of motion. Specifically, each bracket is capable of adjustment in at least three and, preferably, all of vertical, lateral and mesio/distal translational planes of motion and tip, torque and circular rotational planes of motion. Also, the assembly includes an arch wire extending between and retained on the brackets. The arch wire is biased to assume an original neutral configuration but is temporarily deformable from the original neutral configuration for accommodating adjustment of the brackets without the arch wire being removed therefrom.

47 Claims, 14 Drawing Sheets

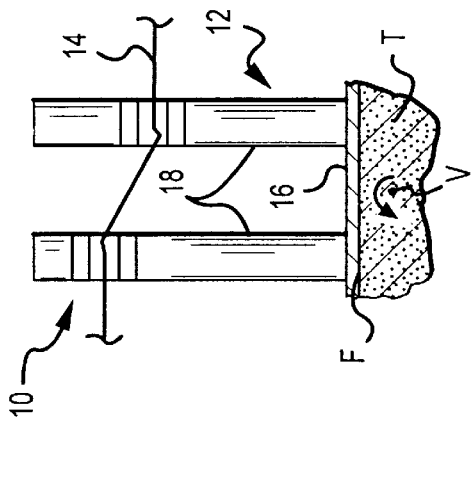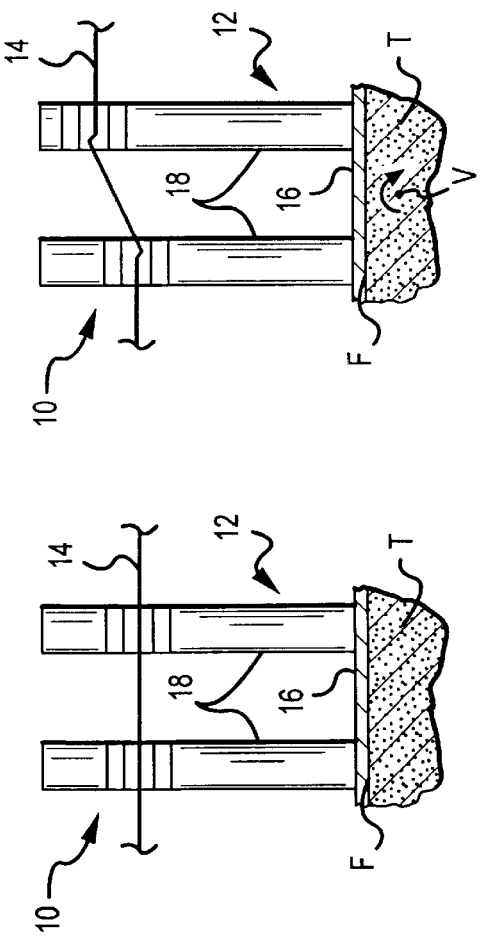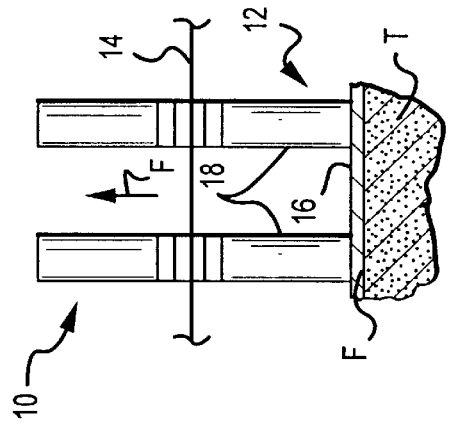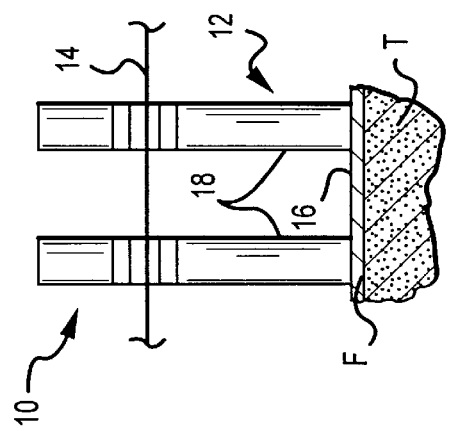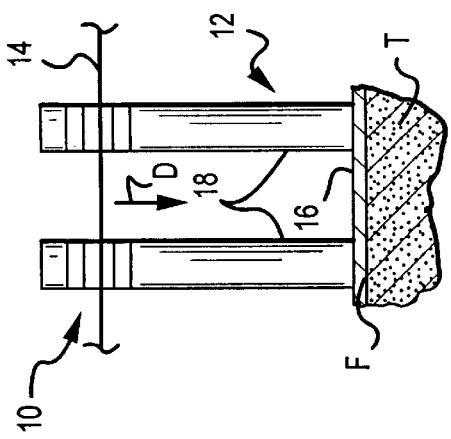

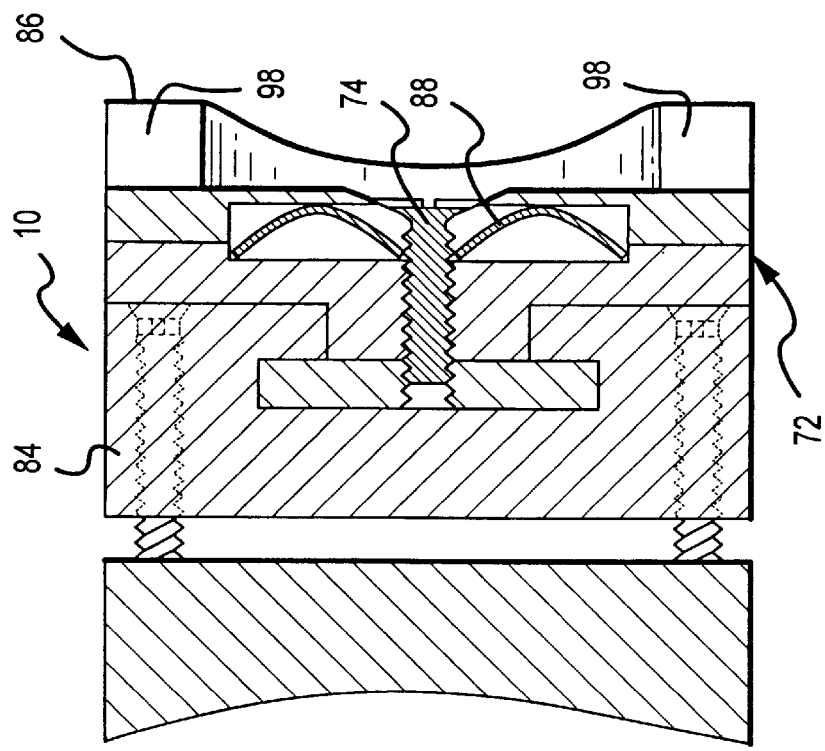
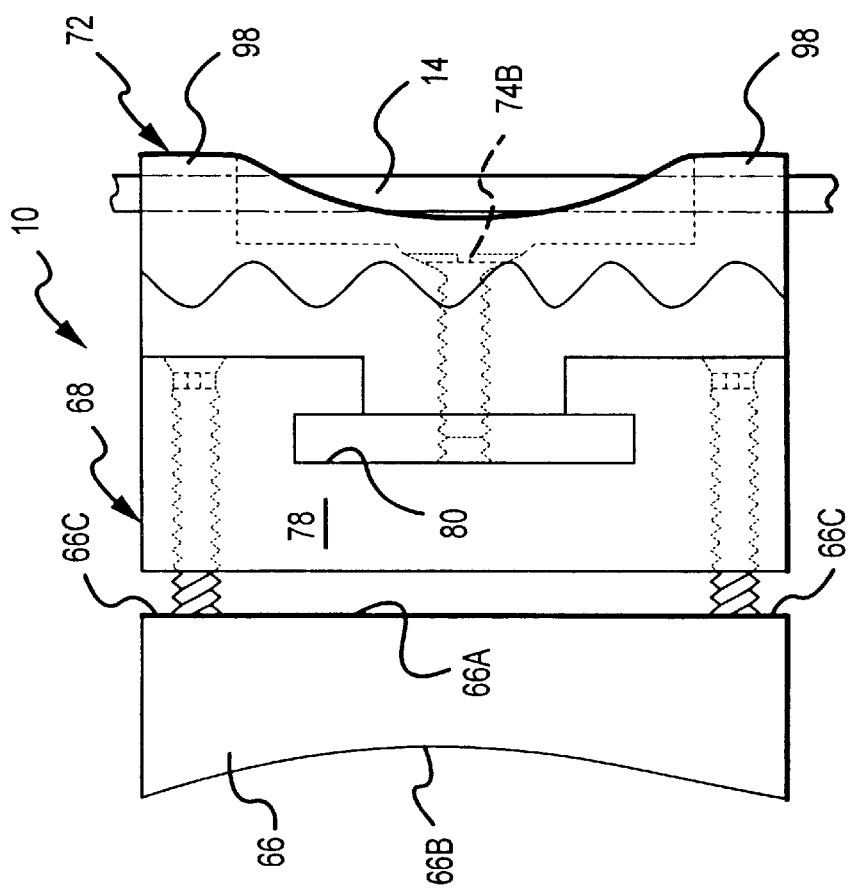

ADJUSTABLE ORTHODONTIC BRACKET ASSEMBLY WITH CONTINUOUS ADJUSTMENT IN ANY ONE OF SIX PLANES OF MOTION

BACKGROUND OF THE INVENTION

1. Field of the Invention

The present invention generally relates to devices used for straightening teeth and, more particularly, is concerned with an adjustable orthodontic bracket assembly with continuous adjustment in any one of six planes of motion.

2. Description of the Prior Art

Orthodontic clinicians practice the art and science of moving teeth into their most optimum position for the use and comfort of patients. Various types of brackets have been employed by clinicians to achieve this task. Generally, anchors and one or more arch wires (so-called because the teeth are setting in upper and lower jaws in the form of an arch) connected to the anchors are secured to the front faces of the teeth. Up to three arch wires may be utilized during the time period in which a patient wears the bracket. The portion of each arch wire at the location of each tooth to be straightened is bent such that forces reactive with the arch wire and a respective anchor attached to the tooth cause the tooth to gradually straighten as desired.

In the past, the clinician had to periodically remove the arch wire and make new bends in it or replace the arch wire with a new one and introduce the new bends in the replacement arch wire to continue the process of straightening the teeth. By removing and placing various bends in the arch wires and using a number of different auxiliaries, the clinician was able to move teeth in six planes of motion, including vertical translational (or up and down) motion, lateral translational motion (or bodily movement of a tooth toward or away from the tongue and palate), mesio/distal translational motion (or bodily movement of a tooth away from or towards the dental midline along the dental arch, the midline being the arch formed by the alignment of the upper and lower teeth), tip rotational motion about an axis extending perpendicular to front surface of tooth (or movement of the root or crown of the tooth toward and away from the midline in the plane tangent to the dental arch), torque rotational motion about an axis extending side to side through tooth (or movement of the root or crown of the tooth toward or away from the tongue or palate) and circular rotational motion about a tooth's longitudinal axis (extending vertically through tooth) in a clockwise or counterclockwise direction. The bending of the arch wire into a configuration to achieve a desired movement of the teeth, however, can be an imprecise way of straightening teeth as it has a high degree of dependency on trial and error which is influenced by the level of skill of the individual clinician.

A variety of orthodontic bracket assemblies have been developed over the years toward overcoming the above-mentioned problems. Representative examples of these orthodontic bracket assemblies are disclosed in U.S. Pat. No. 3,256,602 to Broussard et al., U.S. Pat. No. 3,721,005 to Cohen, U.S. Pat. No. 4,243,387 to Prins, U.S. Pat. No. 4,353,692 to Karrakussoglu, U.S. Pat. No. 4,487,581 to Adler, U.S. Pat. No. 4,496,317 to Hulsey, U.S. Pat. No. 4,597,739 to Rosenberg, U.S. Pat. No. 4,669,980 to Degnan, U.S. Pat. No. 4,676,746 to Klapper, and U.S. Re. Pat. No. 34,044 to Broussard. Problems exist, however, with these and other prior art assemblies, as well. Some prior art assemblies are complex in their design and/or use. Some prior art assemblies require removal of the arch wire to affect changes in orientation of teeth during treatment. None of the prior art assemblies incorporate more than two motion changes in a way in which movements are continuous and independent. In some prior art assemblies it is impossible to adjust movement of the tooth in some of the six planes without causing undesired movements in other planes. Some prior art assemblies allow for movement of the arch wire in up to five of the six planes of motion, but these assemblies also require replacement of parts or removal of the arch wire. Some prior art assemblies are also made of an array of relatively small interchangeable elements, and in many cases several of the six planes of motion are accomplished only with an interchangeable part such that the practical number of different parts needed to accomplish all six motions is quite large.

Consequently, a need still exists for an assembly which provides a solution to the aforementioned problems in the prior art without introducing any new problems in place thereof.

SUMMARY OF THE INVENTION

The present invention provides an adjustable orthodontic bracket assembly designed to satisfy the aforementioned need. The adjustable orthodontic bracket assembly of the present invention allows continuous adjustment in any one of six planes of space. The adjustable bracket assembly is relatively simple in its design and use. Also, the adjustable bracket assembly does not require the use of interchangeable parts nor the removal of the arch wire during treatment. Adjustment of the brackets of the assembly in any one plane of motion can be accomplished without affecting or influencing the adjustment of the brackets in any other plane of motion.

Accordingly, the present invention is directed to an adjustable orthodontic bracket assembly which comprises: (a) a plurality of brackets each attachable to a front face of a tooth such that the bracket is positionable in series relation to one or more other of the brackets; (b) each of the brackets being connectable with an arch wire and without replacement of any parts of the bracket being continuously adjustable in at least three planes of motion. Preferably, each of the brackets is continuously adjustable in six planes of motion wherein adjustment in one of the planes of motion can be accomplished without affecting the adjustment of the bracket in any of the other planes of motion. Specifically, each bracket is capable of at least three of vertical translational motion, lateral translational motion, mesio/distal translational motion, tip rotational motion, torque rotational motion and circular rotational motion.

The assembly further comprises an arch wire extending between the brackets in the series relation to one another and mounted to each bracket. The arch wire is biased to assume an original neutral configuration but is temporarily deformable from the original neutral configuration for accommodating the adjustment of the brackets without the arch wire being removed therefrom. More particularly, the arch wire is made of a material which biases the arch wire to assume the original neutral configuration but allows the arch wire to be temporarily deformed by adjustment of the brackets for causing the deformed arch wire to apply corrective forces on the brackets as the arch wire returns to the original neutral configuration such that over time the arch wire causes the teeth to which the brackets are mounted to move in the direction of the original neutral configuration of the arch wire.

In a first embodiment, each bracket includes a base member, one or a pair of upper horizontal posts, one or a pair of lower horizontal posts, one or a pair of middle vertical posts, one or a pair of lower couplers, one or a pair of upper couplers and one or a pair of retaining nuts. The base member has opposite front and back surfaces. The back surface is attached to the front face of the tooth. The upper horizontal post is fixedly attached to the front surface of the base member and extends outwardly in substantially perpendicular relation thereto. The lower horizontal post is fixedly attached to the front surface of the base member below and extends in substantially parallel relation to the upper horizontal post and outwardly in substantially perpendicular relation to the base member. The middle vertical post has opposite upper and lower ends. The lower coupler is movably mounted to the lower horizontal post such that the lower coupler is movable along the lower horizontal post toward and away from the base member. Also, the lower coupler is pivotally connected to the lower end of the middle vertical post. The upper coupler is movably mounted to the upper horizontal post such that the upper coupler is movable along the upper horizontal post toward and away from the base member. Also, the upper coupler is pivotally connected to the upper end of the middle vertical post. The retaining nut defines a groove for receiving the arch wire and is mounted to the middle vertical post for undergoing movement between the upper and lower ends of the middle vertical post. The middle vertical post has a pair of spring-loaded end caps each mounted to one of the upper and lower ends thereof and allowing for variation of the length of the middle vertical post as the middle vertical post is moved with the upper and lower couplers along the upper and lower horizontal posts.

In a second embodiment, each bracket is in the form of a flexure element comprised of a resiliently deformable material. The bracket includes a base member, one or a pair of spaced apart rear members, one or a pair of spaced apart front members, a pair or plurality of adjustment screws, one or a pair of middle vertical posts and one or a pair of retaining nuts. The base member has opposite front and back surfaces. The back surface is cemented to the front face of the tooth. The rear member has opposite upper and lower ends. One of the upper and lower ends of the rear member has a rearward connection with the base member that spaces the rear member forwardly from the base member and defines a rear slot therebetween adjustable in cross-sectional size as the rear member is flexed via the rearward connection toward and away from the base member. The front member has opposite upper and lower ends. The other of the upper and lower ends of the rear member has a forward connection with a corresponding one of the upper and lower ends of the front member that spaces the front member forwardly of the rear member and defines a front slot therebetween adjustable in cross-sectional size as the front member is flexed via the forward connection toward and away from the rear member. A first of the adjustment screw threads into and extends between each rear member and the base member for flexing the rear member toward and away from the base member upon selected turning of the first adjustment screw relative to the rear and base members. A second of the adjustment screw also threads into and extends between the front and rear members for flexing the front member toward and away from the rear member upon selected turning of the second adjustment screw relative to the front and rear members. The middle vertical post has opposite upper and lower ends and extends between and is mounted at the upper and lower ends thereof to the upper and lower ends of the front member. The retaining nut defines a groove for receiving the arch wire and is mounted to the vertical post for undergoing movement between the upper and lower ends of the vertical post.

In a third embodiment, each bracket is in the form of an adjustable arrangement of multiple stages. The bracket includes a base member, a first stage, a second stage, a third stage, a plurality of adjustment screws and spring means. The base member has opposite front and back surfaces and four corners. The back surface is attachable to the front face of the tooth. The first stage has opposite front and back surfaces and four corners aligned with the four corners of the base member. The first stage and base member define a gap therebetween adjustable in cross-sectional size as the first stage is moved toward and away from the base member. The front surface of the first stage defines a vertical groove having a dovetail configuration. The second stage has a shape substantially conforming to the dovetail configuration of the vertical groove of the front surface of the first stage and slidably fitting therewithin. In one construction, the third stage defines a groove for receiving the arch wire and is rotatably mounted to the second stage. Each of three adjustment screws is threaded into and extends between the first stage and base member at one of the four corners of the first stage and base member for moving the first stage toward and away from the base member upon selected turning of each of the three adjustment screws relative to the first stage and base member. A pair of the adjustment screws are spaced apart from one another and secured through the third stage and threaded into the second stage for adjusting the rotational position of the third stage relative to the second stage upon loosening and tightening the pair of adjustment screws. The spring means extends between and is mounted to the first stage and base member at the fourth of the four corners of the first stage and base member for biasing the first stage toward the base member. In another construction, the third stage has a rear member, a front member and spring means mounting the front and rear members to one another and to the second stage and biasing the front member toward the rear member. Each of the rear and front members defines mateable radial splines such that the front member may be rotated in relation to the rear member by extension of the spring means upon pulling the front member away from the rear member and rotating the front member and by retraction of the spring means upon allowing the front member to fall back into mateable relation with the rear member. The front member defines a groove for receiving an arch wire. Each of four adjustment screws is threaded into and extends between the first stage and base member at one of the four corners of the first stage and base member for moving the first stage toward and away from the base member upon selected turning of each of the adjustment screws relative to the first stage and base member. This construction does not utilize the spring means of the other construction, which is replaced with a fourth adjustment screw.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which:

FIGS. 4A–4F are top schematic views of the first embodiment of the assembly showing one of the brackets of FIG. 2 in various configurations.

FIG. 14 is a top plan view of the alternative construction of the third embodiment of the assembly of FIG. 13.

FIG. 15 is a sectional view on a reduced scale of the assembly taken along line 15—15 of FIG. 13.

DETAILED DESCRIPTION OF THE INVENTION

Figure 1:
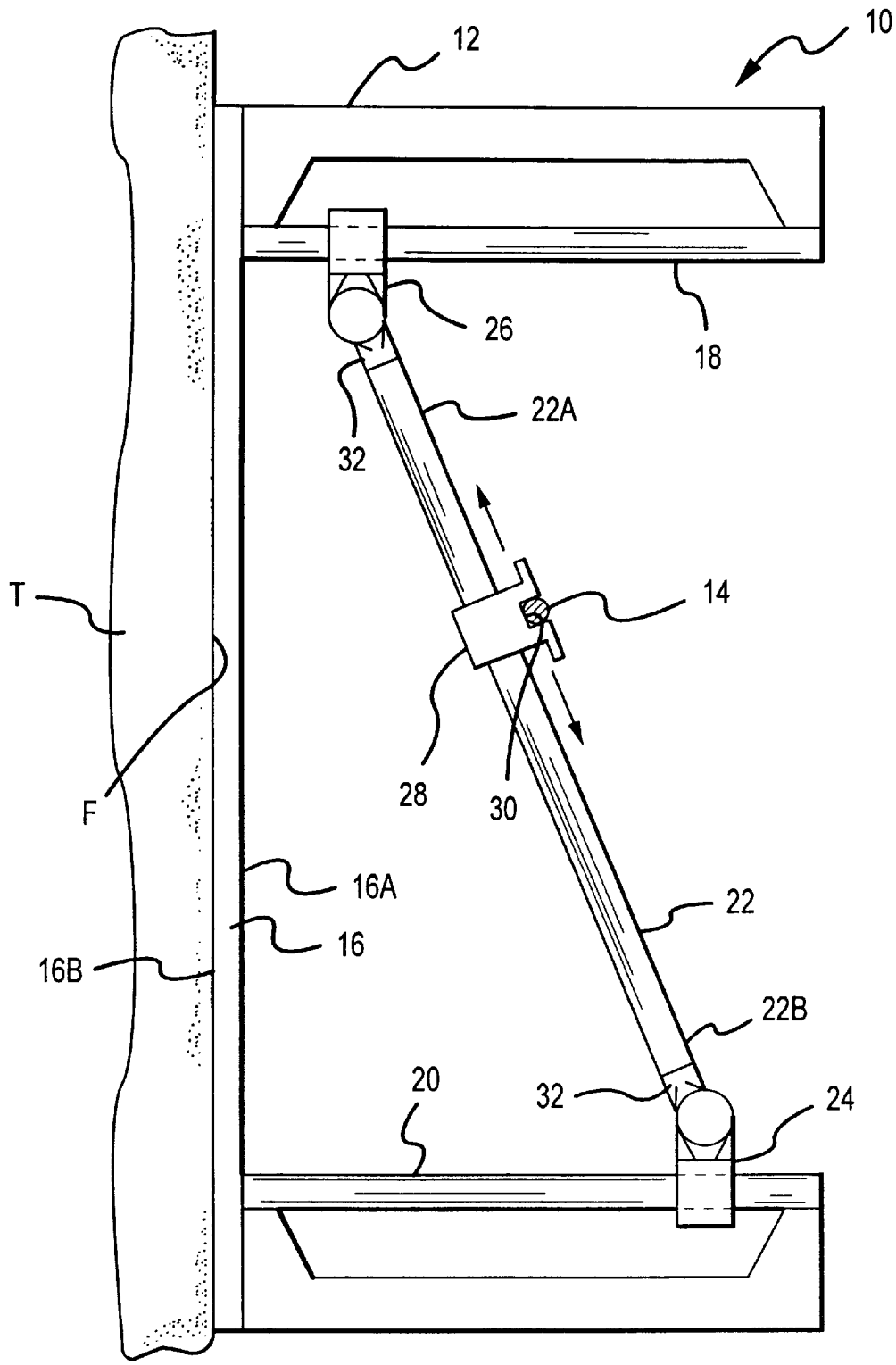
FIG. 1 is a side schematic view of a first embodiment of an adjustable orthodontic bracket assembly of the present invention showing a bracket including a single post arrangement of the assembly.

Referring to the drawings and particularly to FIGS. 1, 3, 6, 11 and 13, there is illustrated three different embodiments of an adjustable orthodontic bracket assembly, generally designated 10, of the present invention. The adjustable orthodontic bracket assembly 10 basically includes a plurality of brackets 12 and an elongated arch wire 14. Each bracket 12 is attachable in any suitable manner, such as by the use of a cement or adhesive, to a front face F of a tooth T such that the bracket 12 is disposed in series relation to one or more other of the brackets 12. The arch wire 14 is connected with each of the brackets 12 and without replacement of any parts each of the brackets 12 is continuously adjustable in at least three planes of motion and, preferably, in six planes of motion wherein an adjustment in any one of the planes of motion can be accomplished without affecting or influencing the adjustment of the bracket 12 in any of the other planes of motion.

Figure 2:
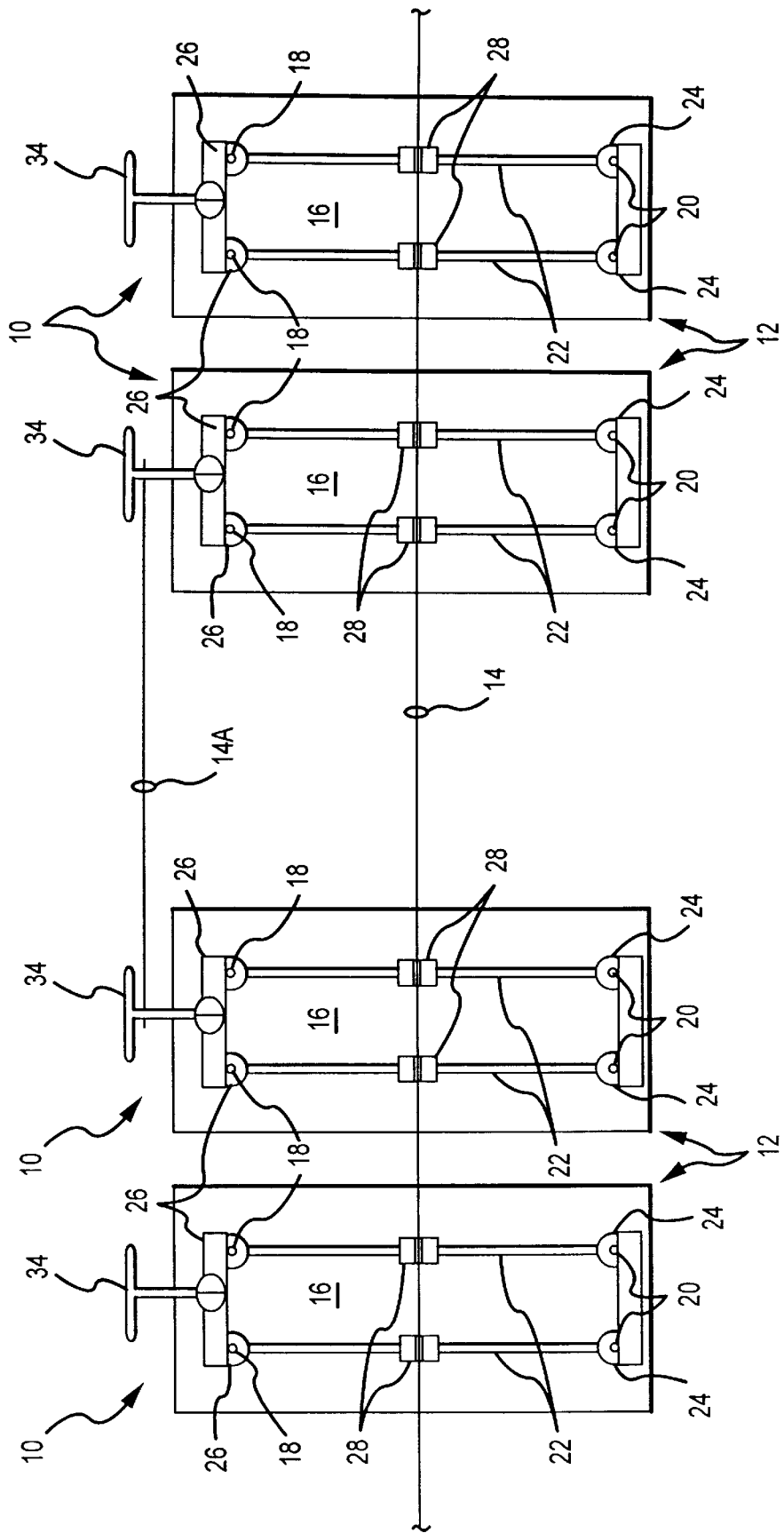
FIG. 2 is a front schematic view of the first embodiment of the adjustable orthodontic bracket assembly showing each of a plurality of brackets including a pair of post arrangements of the assembly.
Figure 3:
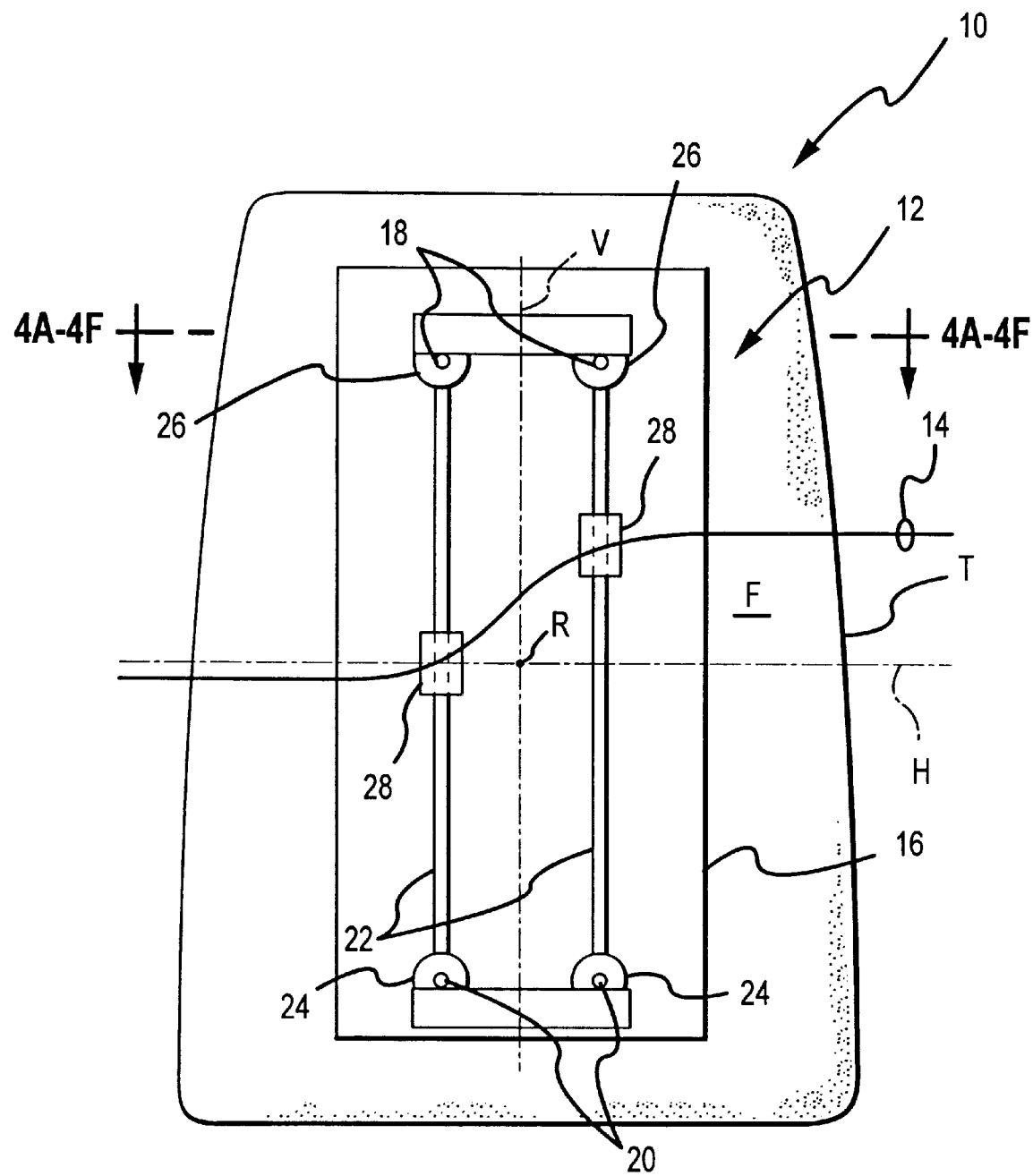
FIG. 3 is a front schematic view of the first embodiment of the assembly showing one of the brackets of FIG. 2.
Figure 5:
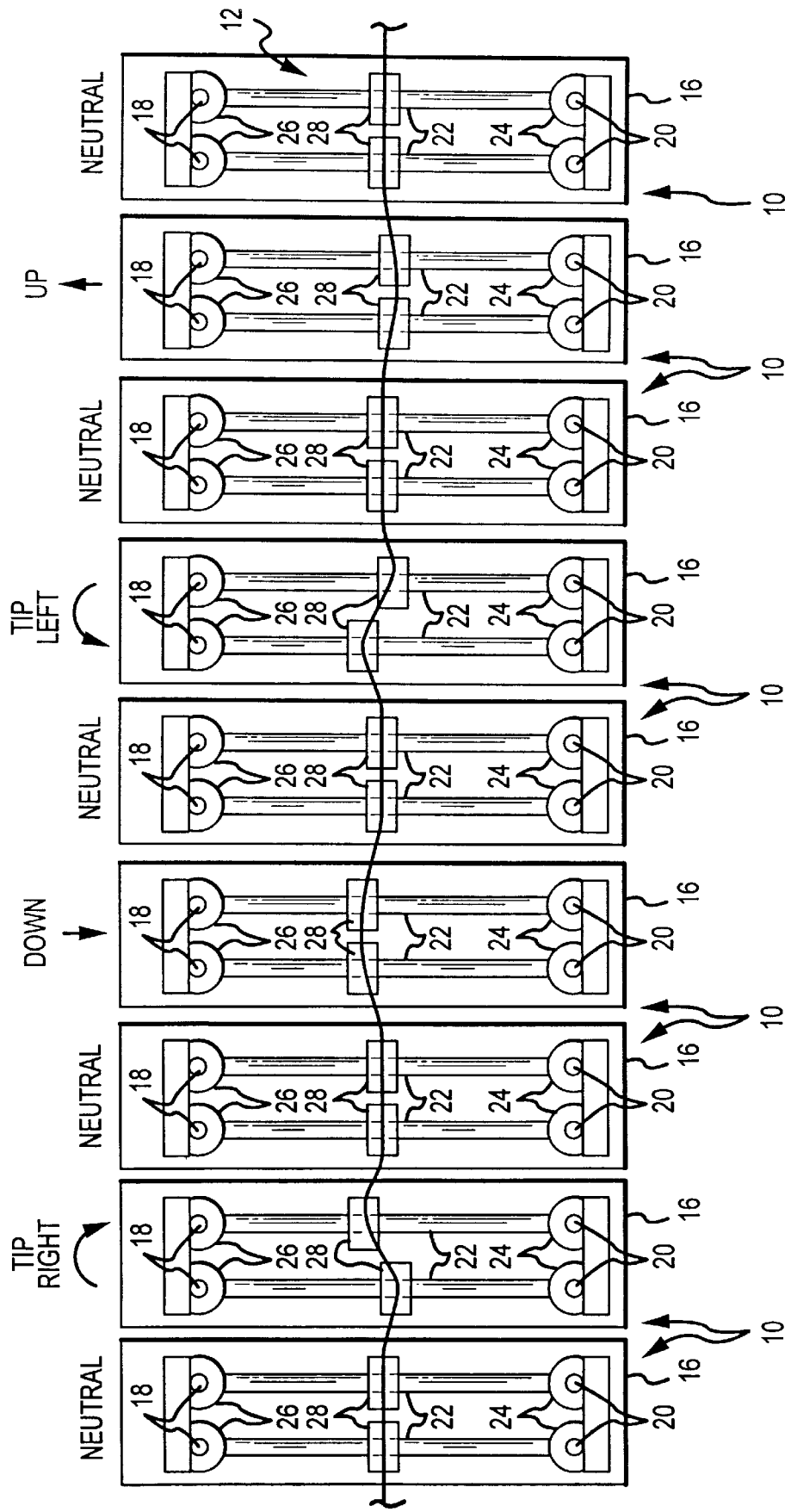
FIG. 5 is a front schematic view of the first embodiment of the assembly showing a plurality of the brackets of FIG. 2 in various configurations.
Figure 7A:
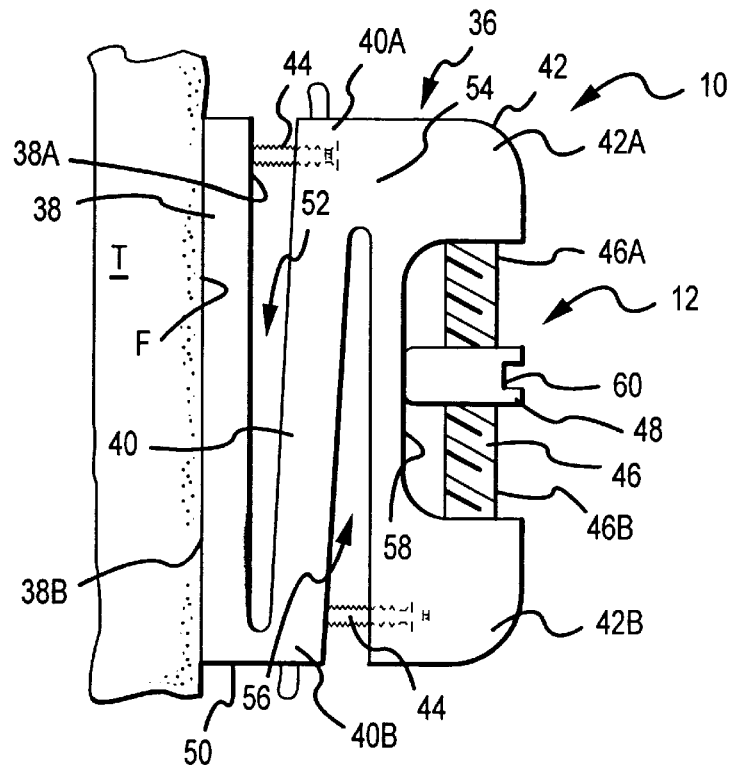
FIG. 7A is a side elevational view of the second embodiment of the assembly shown in FIG. 6.
Figure 7B:
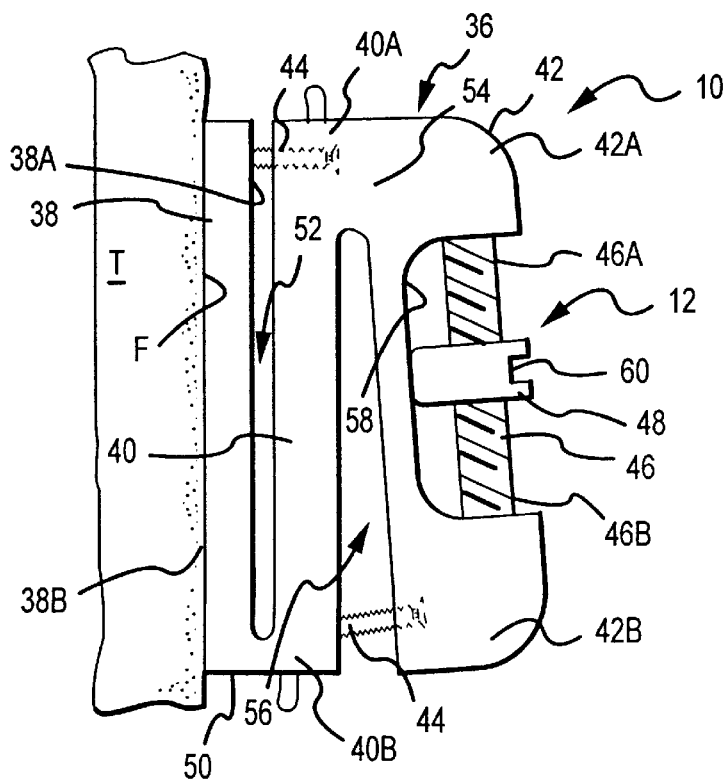
FIG. 7B is a side elevational view of the second embodiment of the assembly shown adjusted into a configuration different from that of FIG. 7A.
Figure 8:
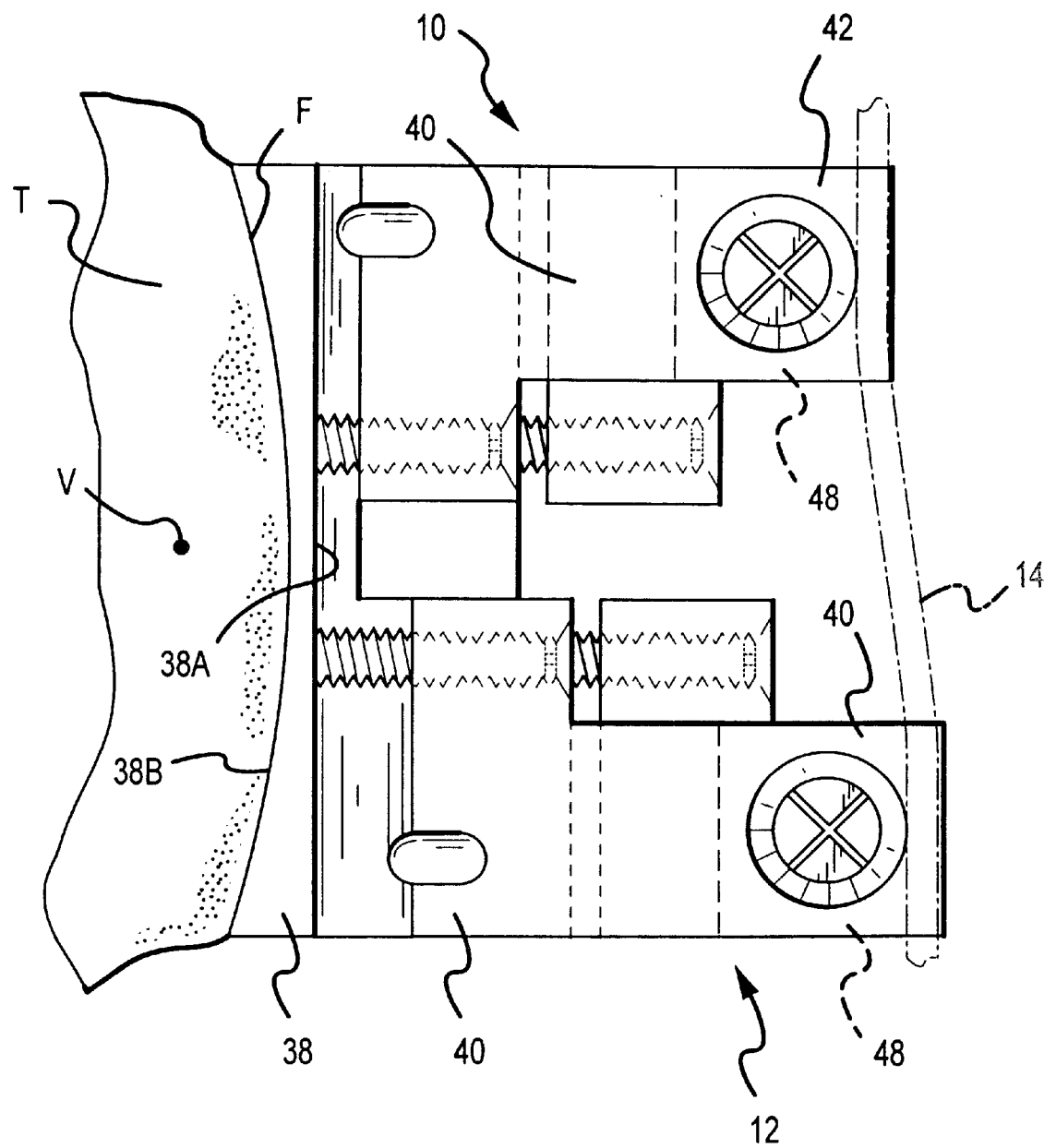
FIG. 8 is a top plan view of the second embodiment of the assembly.
Figure 9:
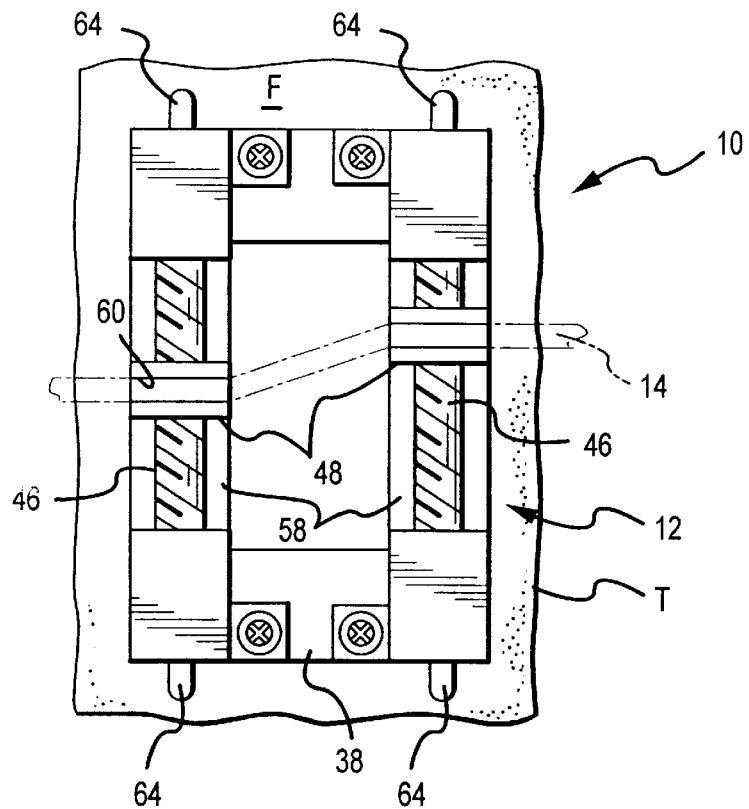
FIG. 9 is a front elevational view of the second embodiment of the assembly.
Figure 10:
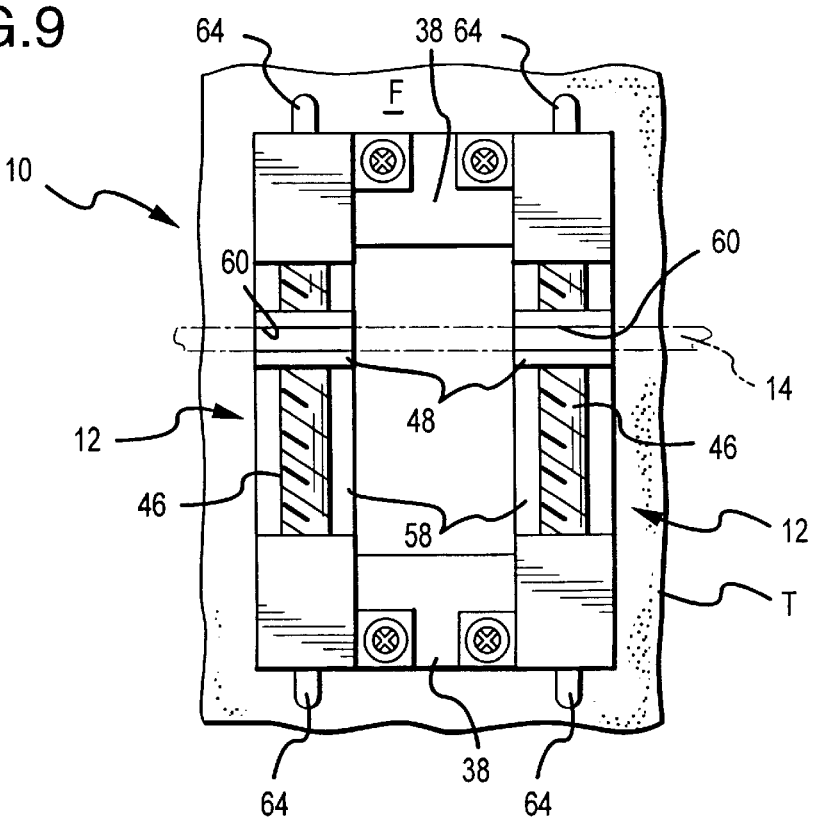
FIG. 10 is a front elevational view of the second embodiment of the assembly shown adjusted into a configuration different from that of FIG. 9.

Specifically, the planes of motion in which each bracket 12 is capable of adjustment are conventionally well-known as vertical translational motion, lateral translational motion, mesio/distal translational motion, tip rotational motion, torque rotational motion and circular rotational motion. FIG. 1 shows the bracket assembly 10 set for inducing a torque rotational motion in the tooth T. FIG. 2 shows an extraction case for mesio/distal translational motion. FIG. 3 shows a vertical rotational axis V about which the bracket assembly 10 will undergo circular rotational motion, a horizontal rotational axis H about which the bracket assembly 10 will undergo torque rotational motion, and a front to rear rotational axis R about which the bracket assembly 10 will undergo tip rotational motion. FIGS. 4A and 4E respectively show the bracket assembly 10 set in a neutral state. FIGS. 4B and 4C respectively show the bracket assembly 10 set for clockwise and counterclockwise circular rotational motions of the teeth T about vertical rotational axes V. FIGS. 4D and 4F respectively show the bracket assembly 10 set for lateral translational motions toward and away from the dental arch in the directions of the respective arrows D and F. FIG. 5 carries labels and arrows showing various ones of the translational and rotational motions as well as neutral conditions. FIG. 7A shows the bracket assembly 10 set for lateral translational motion or in back and front directions. FIG. 7B shows the bracket assembly 10 set for torque rotational motion about a side-to-side rotational axis H. FIG. 8 shows the bracket assembly 10 set for circular rotational motion about vertical axis V. FIG. 9 shows the bracket assembly 10 set for tip rotational motion while FIG. 10 shows the bracket assembly 10 set for vertical translational motion.

The arch wire 14 extends between the brackets 12 in the series relation to one another and is connected to each bracket 12 by a retaining member. The arch wire 14 is biased to assume an original neutral configuration substantially conforming to the configuration of the normal dental arch but the arch wire 14 is temporarily deformable from the original neutral configuration for accommodating the adjustment of the brackets 12 without the arch wire 14 being removed therefrom. More particularly, the arch wire 14 is made of any suitable material which biases the arch wire 14 to assume the original neutral configuration (FIG. 2) but allows the arch wire 14 to be temporarily deformed (FIG. 5) by the adjustment of the respective brackets 12 for causing the deformed arch wire 14 to apply corrective forces on the brackets 12 as the arch wire 14 returns to the original neutral configuration such that over time the arch wire 14 causes the teeth to which the brackets 12 are attached to also move to the desired corrected positions.

Referring now to FIGS. 1 to 5, there is illustrated a first embodiment of the adjustable bracket assembly 10 wherein each bracket 12 includes a base member 16, an adjustment mechanism comprising one or a pair of upper horizontal posts 18, one or a pair of lower horizontal posts 20, one or a pair of middle vertical posts 22, one or a pair of lower couplers 24, and one or a pair of upper couplers 26, and one or a pair of retaining members or nuts 28. The base member 16 has opposite front and back surfaces 16A, 16B. The back surface 16B is attached, such as by being bonded or cemented, to the front face F of the tooth T. The upper horizontal post 18 is fixedly attached to the front surface 16A of the base member 16 and extends outwardly therefrom in a substantially perpendicular relation thereto. The lower horizontal post 20 is fixedly attached to the front surface 16A of the base member 16 below and extends in substantially parallel relation to the upper horizontal post 18 and outwardly therefrom in a substantially perpendicular relation to the base member 16. The middle vertical post 22 has opposite upper and lower ends 22A, 22B.

The lower coupler 24 is movably mounted to the lower horizontal post 20 such that the lower coupler 24 is movable along the lower horizontal post 20 toward and away from the base member 16. Also, the lower coupler 24 is pivotally connected to the lower end 22B of the middle vertical post 22. The upper coupler 26 is movably mounted to the upper horizontal post 18 such that the upper coupler 26 is movable along the upper horizontal post 18 toward and away from the base member 16. Also, the upper coupler 26 is pivotally connected to the upper end 22A of the middle vertical post 22. The retaining nut 28 defines a groove 30 for receiving the arch wire 14 and is mounted to the middle vertical post 22 for undergoing movement between the upper and lower ends 22A, 22B of the middle vertical post 22.

If the bracket 12 includes only a single post arrangement, as shown particularly in FIG. 1, then the bracket 12 is only adjustable in three orthogonal planes of motion. However, if the bracket 12 includes the pair of post arrangements, as shown particularly in FIGS. 2 to 5, the bracket 12 is adjustable in six planes of motion. Each member of a pair is spaced from and horizontally aligned with the other member of the pair comprising the bracket 12.

More particularly, the base member 16 has a substantially rectangular configuration, though may have any other suitable shape. The base member 16 is comprised of any suitable material which is pliable enough to conform to the front face F of the tooth T but is rigid enough to withstand forces in each of the six planes of motion once attached to the tooth T. Any suitable type of adhesive or cement may be used in attaching the base member 16.

The upper horizontal post 18 has a substantially cylindrical configuration, though may have any other suitable shape, allowing the upper coupler 26 to be slidably or threadably moved therealong. The upper horizontal post 18 is comprised of a substantially rigid material able to withstand forces in each of the six planes of motion once assembled. The upper horizontal post 18 has a length of any suitable size. The lower horizontal post 20 has a substantially cylindrical configuration, though may have any other suitable shape, allowing the lower coupler 24 to be slidably or threadably moved therealong. The lower horizontal post 20 is comprised of a substantially rigid material able to withstand forces in each of the six planes of motion once assembled. The lower horizontal post 20 has a length of any suitable size but is, most advantageously, substantially the same as the length of the upper horizontal post 18. The upper and lower horizontal posts 18, 20 are spaced apart from one another any suitable distance, though each of the upper and lower horizontal posts 18, 20 is generally intended to be mounted closer to the top or bottom ends, respectively, of the base member 16 than to a middle location thereon.

The middle vertical post 22 has a substantially cylindrical configuration, though may have any other suitable shape, allowing the retaining nut 28 to be slidably or threadably moved therealong. The middle vertical post 22 is comprised of a substantially rigid material able to withstand forces in each of the six planes of motion once assembled. The middle vertical post 22 has a length of any suitable size but which is adjustable. The middle vertical post 22 further has a pair of spring-loaded end caps 32. Each spring-loaded end cap 32 is mounted to one of the upper and lower ends 22A, 22B thereof and allows for variation of the length of the middle vertical post 22 as the middle vertical post 22 is moved with the lower and upper couplers 24, 26 along the upper and lower horizontal posts 18, 20.

The lower coupler 24 has a substantially annular configuration, though may have any other suitable shape. The lower coupler 24 conforms to the configuration of the lower horizontal post 20 such that the lower horizontal post 20 fits through the lower coupler 24 and such that the lower coupler 24 is movable therealong. The lower coupler 24 pivotally mounts the spring-loaded end cap 32 at the lower end 22B of the middle vertical post 22.

The upper coupler 26 has a substantially annular configuration, though may have any other suitable shape. The upper coupler 26 conforms to the configuration of the upper horizontal post 18 such that the upper horizontal post 18 fits through the upper coupler 26 and such that the upper coupler 26 is movable therealong. The upper coupler 26 pivotally mounts the spring-loaded end cap 32 at the upper end 22A of the middle vertical post 22. The lower and upper couplers 24, 26 are identical, though need not be so limited. Each of the lower and upper couplers 24, 26 may be rotated or otherwise adjusted in one direction or way to allow movement thereof along the lower and upper horizontal posts 20, 18, respectively, and rotated or otherwise adjusted in another direction or way to cause the lower and upper couplers 24, 26 to be secured in place at a selected position along the lower and upper horizontal posts 20, 18.

The retaining nut 28 has a substantially annular configuration, though may have any other suitable shape. The retaining nut 28 conforms to the configuration of the middle vertical post 22 such that the middle vertical post 22 fits through the retaining nut 28 and such that the retaining nut 28 is movable therealong. The retaining nut 28 may be rotated or otherwise adjusted in one direction or way to allow movement thereof along the middle vertical post 22 and rotated or otherwise adjusted in another direction or way to cause the retaining nut 28 to be secured in place at a selected position along the middle vertical post 22. The arch wire groove 30 is defined on the retaining nut 28 such that the groove 30 faces away from the base member 16. The groove 30 is in disposed in substantially parallel relation to the upper and lower horizontal posts 18, 20. The groove 30 has any suitable size to tightly receive the arch wire 14 therein but its edges are rounded to decrease friction between the arch wire 14 and the groove 30.

Each bracket 12 may further include a plurality of hooks 34, as shown particularly in FIG. 2. Each hook 34 is mounted to the front face 16A of the base member 16 of a bracket 12 between upper horizontal posts 18 or in any other suitable location on the base member 16. Each hook 34 is comprised of a substantially flexible material, though need not be so limited, and is intended to retain a supplemental arch wire 14A extending between brackets 12. The supplemental arch wire 14A is in addition to the main arch wire 14 extending between the retaining nuts 28 of the brackets 12. The hooks 34 are generally aligned horizontally with other hooks 34.

By moving the retaining nut 28 vertically along the vertical post 22 or through vertical translational motion, it is possible to cause the tooth to move in the opposite direction. The retaining nut 28 can be moved to provide lateral translational motion (in and out motion) if both upper and lower couplers 26, 24 on the upper and lower horizontal posts 18, 20 are moved together. If the upper and lower couplers 26, 24 are moved in opposite directions, the bracket 12 causes rotation of the arch wire 14 and create a torque rotational motion on the tooth T. This motion is shown in FIG. 1. Thus, with one bracket 12 three of the six planes of motion can be induced in the tooth. The other plane of translational motion, that is mesio-distal translation, can be obtained by attaching the supplemental wire 14A between the flexible hooks 34 on the teeth adjacent to an extraction site, as seen in FIG. 2. These hooks 34 can be rotated to put a continuously adjustable amount of stress into the hook to provide the mesio-distal translational motion. Thus, with the bracket 12 of FIG. 1, all three translational planes of motion and one rotational plane (torque) of motion can be realized.

In order to provide motion in the other two rotational planes, it is necessary to provide the bracket of FIG. 3 called a siamese design having two post assemblies. Each half (or post assembly) of the bracket 12 can be adjusted independently of the other. By adjusting one post assembly vertically up and the other vertically down, the tooth can be rotated about the axis R perpendicular to the front surface F of the tooth T causing tip rotational motion of the tooth. By adjusting one post assembly toward the front surface F of the tooth T and the other post assembly away from the front surface F of the tooth T, the tooth T can be rotated around the longitudinal or vertical axis V of the tooth causing circular rotational motion. The siamese bracket design is an example of an adjustable bracket assembly that allows continuous adjustment of the tooth in all of the six planes of motion. Furthermore, the bracket can be adjusted without removing the arch wire 14 and requires no additional or interchangeable pieces.

Referring now to FIGS. 6 to 10, there is illustrated a second embodiment of the assembly 10 wherein each bracket 12 comprises an adjustment mechanism that is in the form of a strong spring or flexure element 36 which is comprised of a resiliently deformable material. The flexure assembly of FIG. 6 uses two flexure elements 36 to accomplish the same motions as the post assembly using the flexure elements instead of the posts with sliding or threaded elements. FIGS. 7A and 7B show torque and lateral motions. FIG. 8 shows circular rotational motion about axis V. FIG. 9 shows tip rotational motion and FIG. 10 shows vertical translational motion.

The flexure element 36 includes a base member 38, one or a pair of spaced apart rear members 40, one or a pair of spaced apart front members 42, a pair or plurality of adjustment screws 44, and one or a pair of middle vertical posts 46 and one or a pair of retaining member or nuts 48. The base member 38 has opposite front and back surfaces 38A, 38B. The back surface 38B is attached, such as by being bonded or cemented, to the front face F of the tooth T. The rear member 40 has opposite upper and lower ends 40A, 40B. The lower end 40B of the rear member 40 has a rearward integral connection 50 with the base member 38 that spaces the respective rear member 40 forwardly from the base member 38 and defines a rear slot 52 therebetween adjustable in cross-sectional size as the rear member 40 is flexed via the rearward connection 50 toward and away from the base member 38. Alternatively, the rearward connection 50 can be provided between the upper end 40A of the rear member 40 and the base member 38. The front member 42 has opposite upper and lower ends 42A, 42B. The upper end 42A of the front member 42 has a forward integral connection 54 with the upper end 40A of the rear member 40 that spaces the front member 42 forwardly of the rear member 40 and defines a front slot 56 therebetween adjustable in cross-sectional size as the front member 42 is flexed via the forward connection 54 toward and away from the rear member 40. Alternatively, the forward connection 54 can be provided between the lower end 40B of the rear member 40 and the lower end 42B of the front member 42. The front member 42 further defines a front recess 58 between the upper and lower ends 42A, 42B thereof.

First ones of the adjustment screws 44 are threaded into and extend between each of the rear members 40 and the base member 38 at suitable locations spaced from the rearward connections 50 between the rear and base members 40, 38 and cause flexing of the rear members 40 toward and away from the base member 38 upon selected turning of the first adjustment screws 44 relative to the rear and base members 40, 38. Second ones of the adjustment screws 44 are threaded into and extend between each of the front and rear members 42, 40 at suitable locations spaced from the forward connections 54 between the front and rear members 42, 40 and cause flexing of the front members 42 toward and away from the rear members 40 upon selected turning of the second adjustment screws 44 relative to the front and rear members 42, 40. The middle vertical post 46 has opposite upper and lower ends 46A, 46B and is disposed within the front recess 58 of the front member 42. The vertical post 46 extends between and is mounted at upper and lower ends 46A, 46B to the upper and lower ends 42A, 42B of the front member 42. The retaining nut 48 defines a groove 60 for receiving the arch wire 14 and is mounted to the vertical post 46 for undergoing movement between the upper and lower ends 46A, 46B of the vertical post 46.

More particularly, the base member 38 has a substantially rectangular configuration, though its back surface 38B has a substantially arcuate configuration which conforms to the curvature of the front face F of the tooth T, though it need not be so limited. Any suitable type of adhesive or cement may be used in attaching the base member 38 to the tooth T. The rear member 40 has a substantially rectangular configuration, though it need not be so limited. The front recess 56 gives the front member 42 a substantially C-shaped configuration, though need not be so limited. If the bracket 12 includes only one front member 42 and one rear member 40, then only a pair of adjustment screws 44 are present. If the bracket 12 includes a pair of each of the front members 42 and rear members 40, then two pairs of adjustment screws 44 are present. The adjustment screws 44 may be of any suitable type. The middle vertical post 46 has a substantially cylindrical configuration, though may have any other suitable shape, and any suitable length, though is limited by the size of the front recess 58.

The retaining nut 48 has a substantially rectangular configuration, though it may have any other suitable shape, and defines a central opening 62 therethrough. The central opening 62 of the retaining nut 48 conforms to the configuration of the middle vertical post 46 such that the middle vertical post 46 fits through the central opening 62 of the retaining nut 48 and such that the retaining nut 48 is movable along the middle vertical post 46. The retaining nut 48 may be rotated or otherwise adjusted in one direction or way to allow movement thereof along the middle vertical post 46 and rotated or otherwise adjusted in another direction or way to cause the retaining nut 48 to be secured in place at a selected position along the middle vertical post 46. The groove 60 is defined on the retaining nut 48 such that the groove 60 faces away from the base member 38. The groove 60 is in substantially perpendicular relation to the middle vertical post 46 and has a suitable size adapted to tightly receive the arch wire 14.

Figure 6:
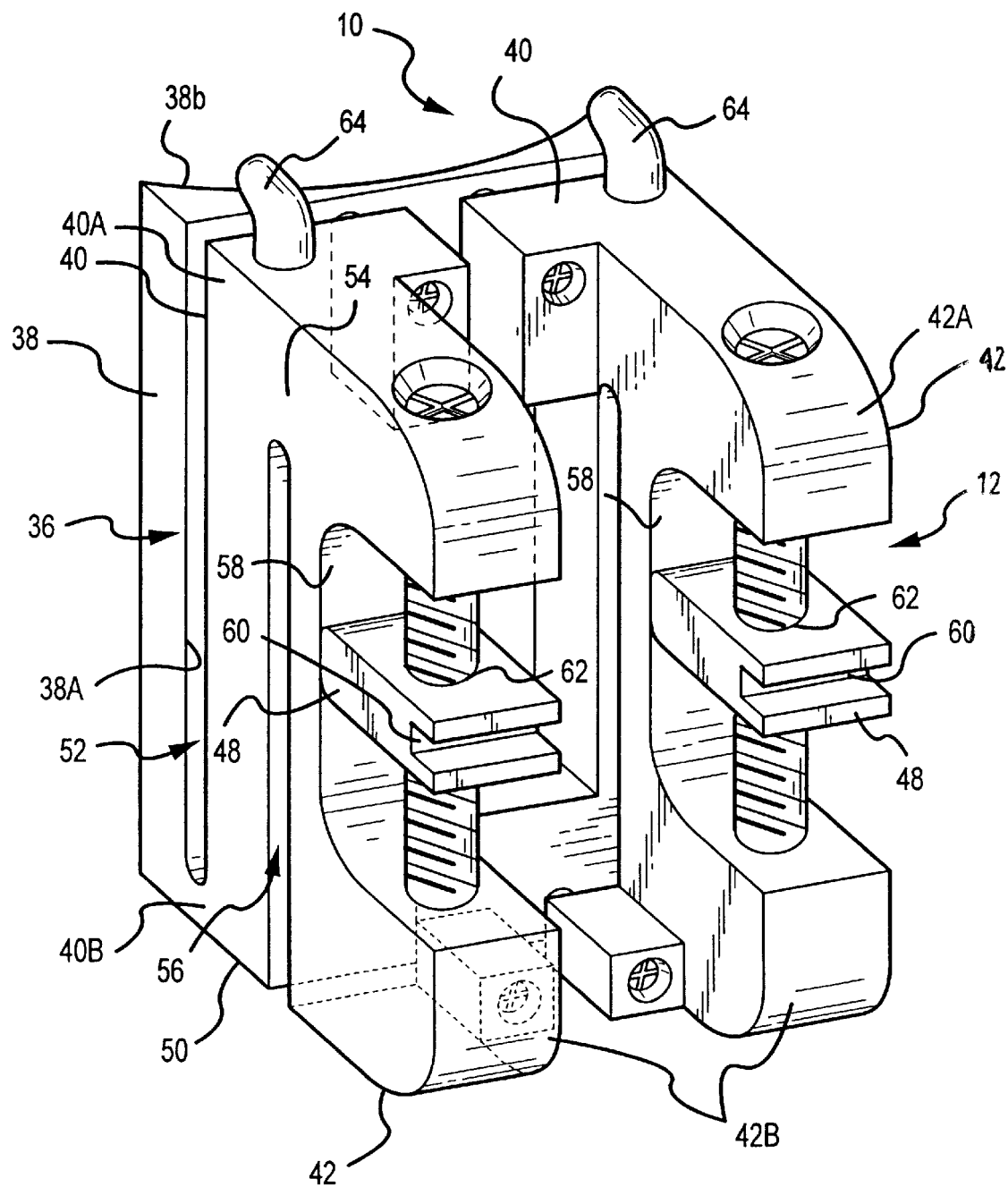
FIG. 6 is a perspective view of a second embodiment of an adjustable orthodontic bracket assembly of the present invention showing a bracket in the form of a flexure element of the assembly.
Figure 6A:
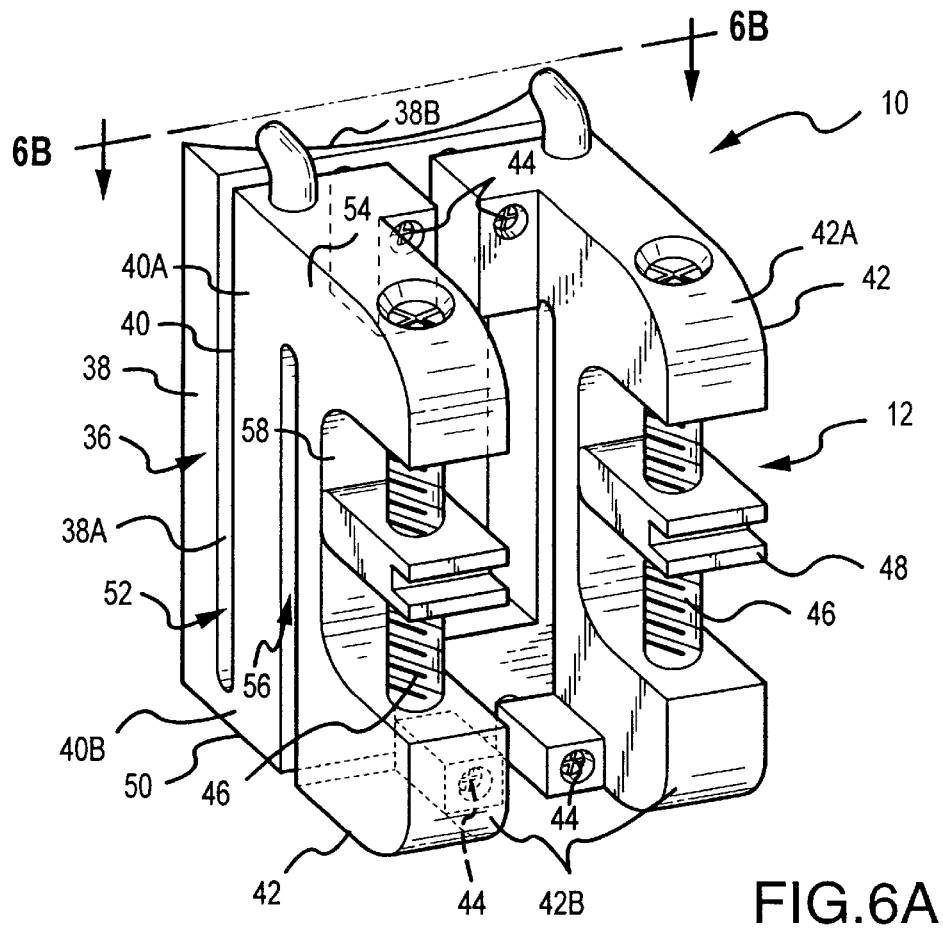
FIG. 6A is a perspective view of the second embodiment of the assembly shown in FIG. 6 on a reduced scale.
Figure 6B:
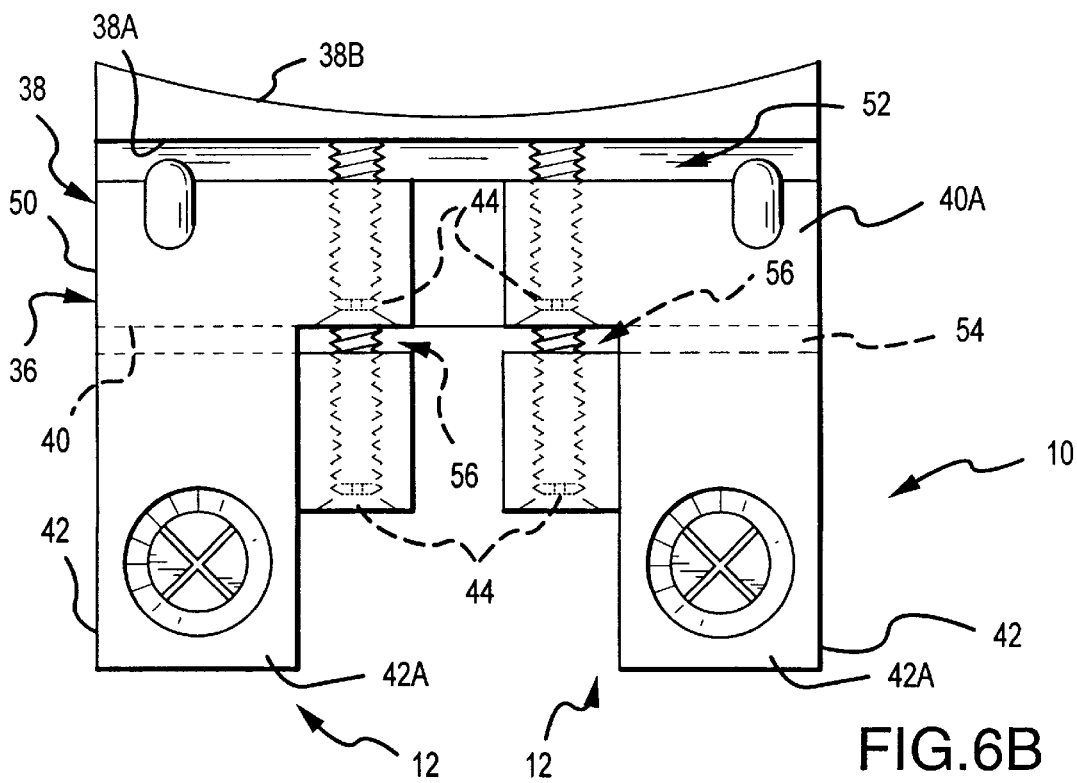
FIG. 6B is a top plan view of the second embodiment of the assembly as seen along line 6B—6B of FIG. 6A.

Each bracket 12 may further include a plurality of hooks 64, as shown particularly in FIGS. 6, 9 and 10. Each hook 64 may be mounted either where the upper ends 40A, 42A of the rear and front members 40, 42 meet or at a forward location on one of the upper and lower ends 42A, 42B of the front member 42 or in any other suitable location. Each hook 64 is comprised of a substantially flexible material, though need not be so limited, and is intended to retain a supplemental arch wire 14A extending between brackets 12. The supplemental arch wire 14A is in addition to the main arch wire 14 extending between the retaining nuts 48 of the brackets 12. The hooks 64 are generally aligned horizontally and/or vertically with other hooks 64.

Referring now to FIGS. 11 to 15, there is illustrated a third embodiment of the assembly 10 wherein each bracket 12 is in the form of an arrangement of multiple stages. The bracket 12 includes a base member 66, an adjustment mechanism comprising a first stage 68, a second stage 70, a third stage 72, a plurality of adjustment screws 74 and spring means 76 and a retaining member. The base member 66 has opposite front and back surfaces 66A, 66B and a plurality of corners 66C such as four in number. The back surface 66B is attached, such as by being bonded or cemented, to the front face F of the tooth T. The first stage 68 has opposite front and back surfaces 68A, 68B and a plurality of corners 68C, such as four in number, aligned with the four corners 66C of the base member 66. The first stage 68 and the base member 66 are spaced apart by a gap 78 therebetween being adjustable in cross-sectional size as the first stage 68 is moved toward and away from the base member 66. The front surface 68A of the first stage 68 defines a vertical groove 80 having a dovetail configuration. The second stage 70 has a shape substantially conforming to the dovetail configuration of the vertical groove 80 of the front surface 68A of the first stage 68 and slidably fitting therewithin.

Figure 11:
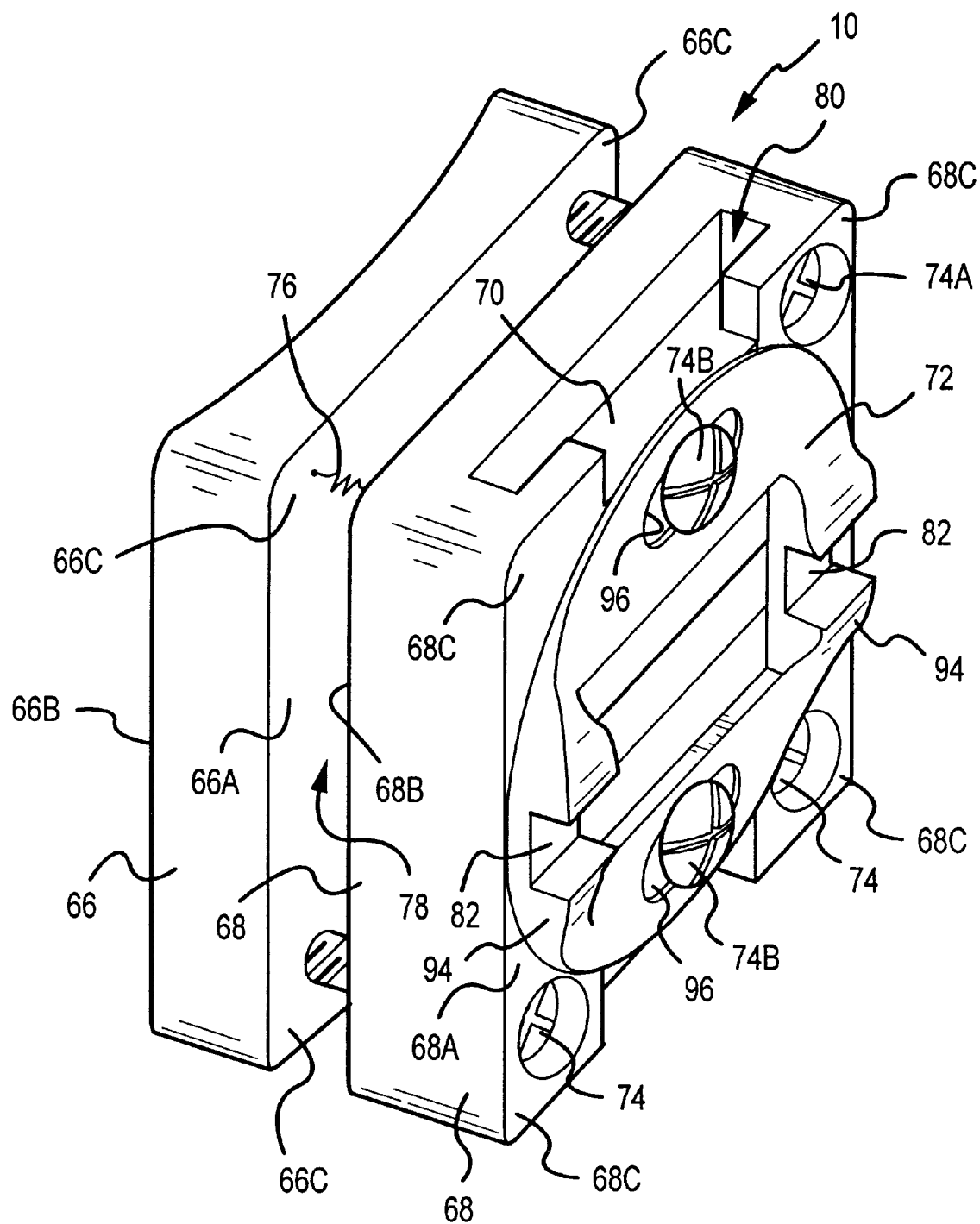
FIG. 11 is a perspective view of a third embodiment of an adjustable orthodontic bracket assembly of the present invention showing a bracket in the form of an adjustable arrangement of multiple stages of the assembly.
Figure 12:
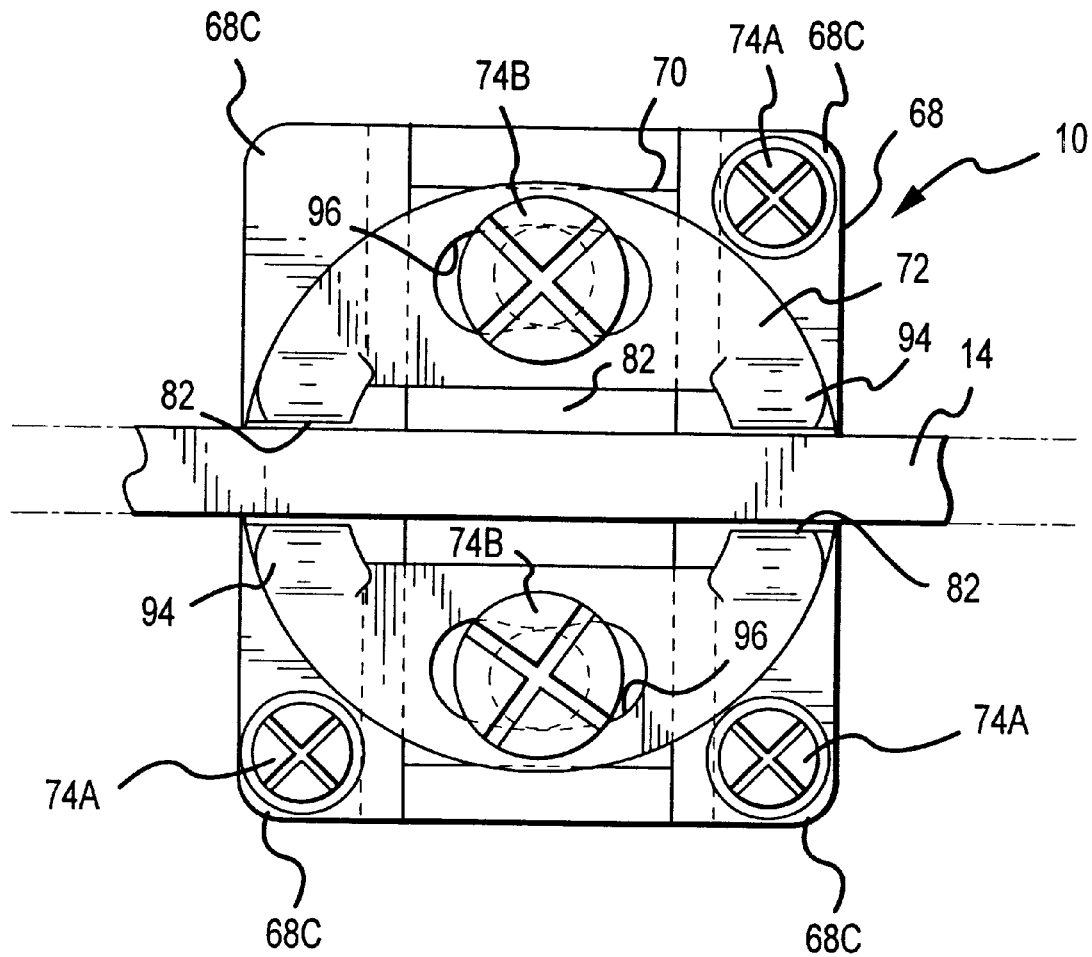
FIG. 12 is a front elevational view of the third embodiment of the assembly shown in FIG. 11.

In one construction of the third embodiment, shown in FIGS. 11 and 12, the third stage 72 is attached to a retaining member which defines a groove 82 for receiving the arch wire 14 and is rotatably mounted to the second stage 70. Each of three adjustment screws 74A is threaded into and extends between the first stage 68 and base member 66 at one of the four corners 68C of the first stage 68 and base member 66 for moving the first stage 68 toward and away from the base member 66 upon selected turning of each of the three adjustment screws 74A relative to the first stage 68 and base member 66. A pair of the adjustment screws 74B are spaced apart from one another and secured through the third stage 72 and threaded into the second stage 70 for adjusting the rotational position of the third stage 72 relative to the second stage 70. The spring means 76 extends between and is mounted to the first stage 68 and base member 66 at the fourth of the four corners 68C of the first stage 68 and base member 66 for biasing the first stage 68 toward the base member 66. An in/out translation is accomplished by lengthening or shortening three legs of the first stage by the same amount. Adjusting the length of an upper right leg, causes the first stage to rotate around the bottom two legs and thereby the tooth to undergo torque rotational motion. Adjusting the bottom left leg rotates the first stage 68 around an axis parallel to the vertical axis V of the tooth providing circular rotational motion of the tooth. The third stage 72 can be rotated to rotate the arch wire 14 about the axis R peripendicular to the base member 66 and front surface F of the tooth T. These moves together can move the tooth through tip rotational motion. The second stage 70 provides orthogonal continuous motion in all three rotational planes and lateral translational motion. The other plane of translational motion, lateral, can be obtained by hooking a supplemental arch wire 14A between the brackets on adjacent teeth, the same as in FIG. 2.

Figure 13:
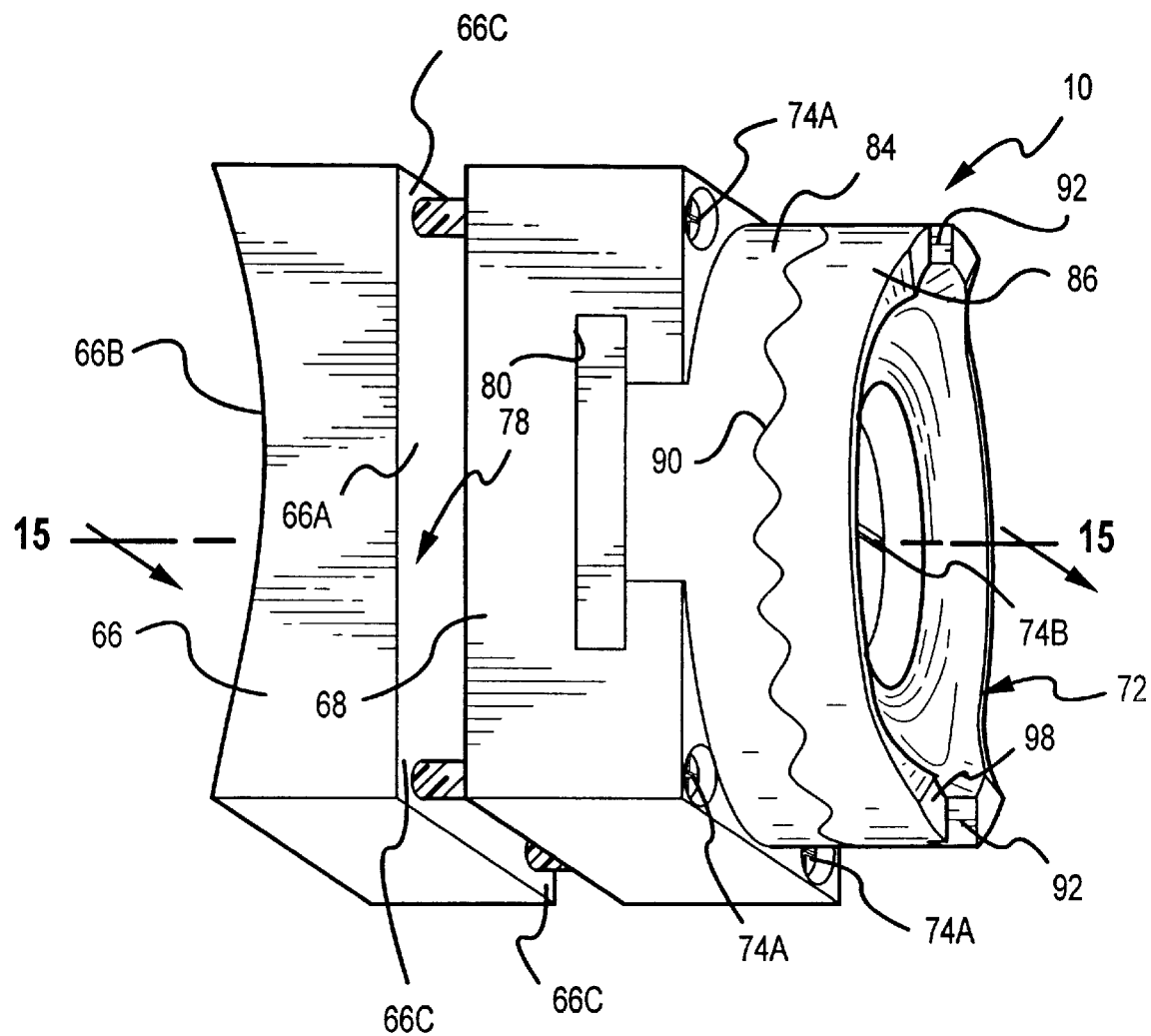
FIG. 13 is a perspective view of an alternative construction of the third embodiment of the assembly shown in FIGS. 11 and 12.

In another construction of the third embodiment, shown in FIGS. 13 to 15, the third stage 72 has a rear member 84, a front member 86 and spring means 88 mounting the front and rear members 86, 84 to one another and to the second stage 70 and biasing the front member 86 toward the rear member 84. Each of the rear and front members 84, 86 defines mateable radial splines 90 such that the front member 86 may be rotated in relation to the rear member 84 by extension of the spring 88 upon pulling the front member 86 away from the rear member 84 and rotating the front member 86 and by retraction of the spring 88 upon allowing the front member 86 to fall back into mateable relation with the rear member 84. The front member 86 is attached to a retaining member which defines a groove 92 for receiving the arch wire 14. Each of four adjustment screws 74A is threaded into and extends between the first stage 68 and base member 66 at one of the four corners 86C of the first stage 68 and base member 66 for moving the first stage 68 toward and away from the base member 66 upon selected turning of each of the adjustment screws 74A relative to the first stage 68 and base member 66. This construction does not utilize the spring means 88, which is replaced with a fourth adjustment screw 74A.

The base member 66 has a substantially rectangular configuration, though the back surface 66B thereof has a substantially arcuate configuration which conforms to the curvature of the front face F of the tooth T, though it need not be so limited. Any suitable type of adhesive or cement may be used in attaching the base member 66 to the tooth T. The first stage 68 has a substantially rectangular configuration, though need not be so limited, but for the groove 80 of dovetail- or T-shape in cross-section which extends vertically between and through top and bottom ends of the first stage 68 and interiorly from the front surface 68A. The second stage 70 has a size substantially less than that of the first stage 68. The second stage 70 further has a substantially T-shaped configuration in transverse cross-section which conforms to the configuration of the dovetail groove 80 and also has a transverse cross-sectional size slightly less than that of the dovetail groove 80 for slidably fitting therewithin. The adjustment screws 74 may be of any suitable type.

In the construction shown in FIGS. 11 and 12, the third stage 72 has a substantially circular and flat configuration, though need not be so limited. The third stage 72 has a pair of opposite relief portions 94 which extend outwardly from opposite sides of the third stage 72 on a surface of the third stage 72 which faces away from the second and first stages 70, 68. Each relief portion 94 has a substantially round configuration, though need not be so limited, and defines a portion of the groove 82 therethrough. The third stage 72 further defines a pair of spaced apart slots 96. Each slot 96 is disposed between the relief portions 94 and on one of opposite sides of the groove 82. Each slot 96 is substantially circumferentially directed, though need not be so limited. The pair of the adjustment screws 74B spaced apart from one another and secured through the third stage 72 and threaded into the second stage 70 pass through the slots 96. Each of these adjustment screws 74B may be unscrewed to allow the third stage 72 to rotate circumferentially and then rescrewed to secure the third stage 72 in place. In the construction shown in FIGS. 13 to 15, each of the rear member 84 and front members 86 of the third stage 72 has a substantially circular configuration, though need not be so limited, and has a size substantially the same as that of the other member 84, 86. The front member 86 has a pair of opposite relief portions 98 which extend outwardly from opposite sides of the front member 86 on a surface of the front member 86 which faces away from the rear member 84. Each relief portion 98 has a substantially flat top, though need not be so limited, and defines a portion of the arch wire groove 92 therethrough.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

We claim:

1. An orthodontic bracket which is adjustable relative to an arch wire to apply force to a tooth without removing the arch wire and without replacing component parts of the bracket, the tooth located in a dental arch, the arch wire extends generally parallel to the dental arch, said bracket deriving corrective forces applied to the tooth from deflection of the arch wire, said bracket being adjustable to obtain forces to move the tooth in three mutually perpendicular translational planes and about three mutually perpendicular rotational axes, a first vertical translational plane being generally perpendicular to the general undeflected extension of the arch wire, a second lateral translational plane being generally vertical and perpendicular to the general undeflected extension of the arch wire, and a third mesio/distal translational plane being generally horizontal and parallel to the general undeflected extension of the arch wire and perpendicular to the first and second planes, a first circular rotational axis being generally vertical and perpendicular to the general undeflected extension of the arch wire, a second tip rotational axis being generally horizontal and parallel to the general undeflected extension of the arch wire and perpendicular to the first axis, and a third torque rotational axis being generally horizontal and perpendicular to the general undeflected extension of the arch wire and perpendicular to the first and second axes, the adjustability of said bracket deriving each force in each translational plane and about each rotational axis independently of any forces derived in the other translational planes and rotational axes, the force derived for movement of the tooth in alignment with the third mesio/distal plane requiring a supplemental element connected to said bracket to apply force generally parallel to the undeflected extension of the arch wire along the first axis, said bracket comprising:

a base member to be connected to a front, outer and mostly vertical surface of the tooth to transfer force to the tooth;

a retaining member to be connected to the arch wire; and an adjustment mechanism interconnecting the base member and the retaining member and moving the retaining member relative to the base member in each of the first, second and third translational planes and in each of the first, second and third rotational axes, the adjustment member moving the retaining member relative to the base member in each of planes and axes independently of movement in the other planes and axes while allowing the retaining member to remain connected to the arch wire and while maintaining the retaining member connected to the base member.

2. An orthodontic bracket as defined in claim 1 wherein the adjustment mechanism is adjustable to obtain a continuous range of translational movement in each of the vertical, lateral and mesio/distal planes.

3. An orthodontic bracket as defined in claim 1 wherein the adjustment mechanism is adjustable to obtain a continuous range of rotational movement about each of the circular, tip and torque axes.

4. An orthodontic bracket as defined in claim 3 wherein the adjustment mechanism is adjustable to obtain a continuous range of translational movement in each of the vertical, lateral and mesio/distal planes.

5. An orthodontic bracket as defined in claim 1 wherein:

the base member having opposite front and back surfaces, said back surface being attachable to the front surface of the tooth; and the adjustment mechanism further comprises:

an upper horizontal post fixedly attached to said front surface of said base member and extending outwardly in substantially perpendicular relation thereto;

a lower horizontal post fixedly attached to said front surface of said base member below and extending in substantially parallel relation to said upper horizontal post and outwardly in substantially perpendicular relation to said base member;

a middle vertical post having opposite upper and lower ends;

a lower coupler movably mounted to said lower horizontal post, said lower coupler movable along said lower horizontal post toward and away from said base member, said lower coupler pivotally connected to said lower end of said middle vertical post;

an upper coupler movably mounted to said upper horizontal post, said upper coupler movable along said upper horizontal post toward and away from said base member, said upper coupler pivotally connected to said upper end of said middle vertical post; and wherein said retaining member comprises:

a retaining nut defining a groove for receiving an arch wire and being mounted to said middle vertical post for undergoing movement between said upper and lower ends of said middle vertical post.

6. The assembly of claim 5 wherein said middle vertical post of each of said brackets has a length and a pair of spring-loaded end caps, each of said spring-loaded end caps being mounted to one of said upper and lower ends of said middle vertical post and allowing for variation of said length of said middle vertical post as said middle vertical post is moved with said upper and lower couplers along said upper and lower horizontal posts.

7. An orthodontic bracket as defined in claim 1 wherein:

the base member having opposite front and back surfaces, said back surface being attached to the front surface of the tooth; and the adjustment mechanism further comprises:

a pair of upper horizontal posts fixedly attached to said front surface of said base member and extending outwardly in substantially perpendicular relation thereto;

a pair of lower horizontal posts fixedly attached to said front surface of said base member below and extending in substantially parallel relation to said upper horizontal posts and outwardly in substantially perpendicular relation to said base member;

a pair of middle vertical posts each having opposite upper and lower ends;

a pair of lower couplers each movably mounted to one of said lower horizontal posts, said lower coupler movable along said lower horizontal post toward and away from said base member, each of said lower couplers being pivotally connected to said lower end of one of said middle vertical posts;

a pair of upper couplers each movably mounted to one of said upper horizontal posts, said upper coupler movable along said upper horizontal post toward and away from said base member, each of said upper couplers being pivotally connected to said upper end of one of said middle vertical posts; and wherein said retaining member comprises:

a pair of retaining nuts each defining a groove for receiving a common arch wire and being mounted to one of said middle vertical posts for undergoing movement between said upper and lower ends of said one middle vertical post.

8. The assembly of claim 7 wherein each of said middle vertical posts of each of said brackets has a length and a pair of spring-loaded end caps, each of said spring-loaded end caps being mounted to one of said upper and lower ends of said middle vertical and allowing for variation of said length of said middle vertical post as said middle vertical post is moved with said upper and lower couplers along said upper and lower horizontal posts.

9. An orthodontic bracket as defined in claim 1 wherein:
the base member having opposite front and back surfaces, said back surface being attached to the front surface of the tooth; and the adjustment mechanism further comprises a flexure element of resiliently deformable material, the flexure element further comprising:
a rear member having opposite upper and lower ends, one of said upper and lower ends having a rearward connection with said base member that spaces said rear member forwardly of said base member and defines a rear slot therebetween adjustable in cross-sectional size as said rear member is flexed via said rearward connection toward and away from said base member;
a front member having opposite upper and lower ends, the other of said upper and lower ends of said rear member having a forward connection with a corresponding one of said upper and lower ends of said front member that spaces said front member forwardly of said rear member and defines a front slot therebetween adjustable in cross-sectional size as said front member is flexed via said forward connection toward and away from said rear member;
a pair of adjustment screws, a first of said adjustment screws being threaded into and extending between said rear and base members for flexing said rear member toward and away from said base member upon selected turning of said first adjustment screw relative to said rear and base members, a second of said adjustment screws being threaded into and extending between said front and rear members for flexing said front member toward and away from said rear member upon selected turning of said second adjustment screw relative to front and rear members;
a vertical post having opposite upper and lower ends and extending between and mounted at said upper and lower ends thereof to said upper and lower ends of said front member; and wherein said retaining member comprises:
a retaining nut defining a groove for receiving an arch wire and being mounted to said vertical post for undergoing movement between said upper and lower ends of said vertical post.

10. The assembly of claim 9 wherein said front member further has a front recess formed between said upper and lower ends thereof, said vertical post being disposed within said front recess of said front member.

11. An orthodontic bracket as defined in claim 1 wherein:
the base member having opposite front and back surfaces, said back surface being attached to the front surface of the tooth; and the adjustment mechanism further comprises a flexure element of resiliently deformable material, the flexure element comprising:
a pair of spaced apart rear members each having opposite upper and lower ends, one of said upper and lower ends of each of said rear members having a rearward connection with said base member that spaces said rear member forwardly of said base member and defines a rear slot therebetween adjustable in cross-sectional size as said rear member is flexed via said rearward connection toward and away from said base member;
a pair of spaced apart front members each having opposite upper and lower ends, the other of said upper and lower ends of each of said rear members having a forward connection with a corresponding one of said upper and lower ends of one of said front members that spaces said front member forwardly of said respective rear member and defines a front slot therebetween adjustable in cross-sectional size as said front member is flexed via said forward connection toward and away from said rear member;
a plurality of adjustment screws, a first pair of said adjustment screws threaded into and extending between said rear and base members for flexing said rear members toward and away from said base members upon selected turning of said adjustment screws of said first pair relative to said rear and base members, a second pair of said adjustment screws threaded into and extending between said front and rear members for flexing said front members toward and away from said rear members upon selected turning of said adjustment screws of said second pair relative to said front and rear members;
a pair of vertical posts each having opposite upper and lower ends and mounted at said upper and lower ends thereof to said upper and lower ends of one of said front members; and wherein said retaining member comprises:
a pair of retaining nuts each defining a groove for receiving a common arch wire and being mounted to one of said vertical posts for undergoing movement between said upper and lower ends of said one of said front members.

12. The assembly of claim 11 wherein each of said front members further has a front recess formed between said upper and lower ends thereof, each of said vertical posts being disposed within said front recess of one of said front members.

13. An orthodontic bracket as defined in claim 1 in the form of an adjustable arrangement of multiple stages and wherein:
the base member having opposite front and back surfaces and four corners, said back surface being attached to the front surface of the tooth; and the adjustment mechanism further comprises:
a first stage having opposite front and back surfaces and four corners aligned with said four corners of said base member, said first stage and said base member defining a gap therebetween adjustable in cross-sectional size as said first stage is moved toward and away from said base member, said front surface of said first stage defining a vertical groove having a dovetail configuration;
a second stage having a shape substantially conforming to said dovetail configuration of said vertical groove of said front surface of said first stage and slidably fitting therewithin;
a third stage attached to the retaining member and defining a groove for receiving an arch wire and being rotatably mounted to said second stage;

a plurality of adjustment screws, each of three of said adjustment screws threaded into and extending between said first stage and base member at one of said four corners of said first stage and base member for moving said first stage toward and away from said base member upon selected turning of each of said three adjustment screws relative to said first stage and base member, a pair of said adjustment screws spaced apart from one another and being secured through said third stage and threaded into said second stage for adjusting the rotational position of said third stage relative to said second stage upon loosening and tightening of said pair of adjustment screws; and spring means extending between and mounted to said first stage and base member at a fourth of said four corners of said first stage and base member for biasing said first stage toward said base member.

14. An orthodontic bracket as defined in claim 1 in the form of an adjustable arrangement of multiple stages and wherein:

the base member having opposite front and back surfaces and four corners, said back surface being attached to the front surface of the tooth; and the adjustment mechanism further comprises:

a first stage having opposite front and back surfaces and four corners aligned with said four corners of said base member, said first stage and said base member defining a gap therebetween adjustable in cross-sectional size as said first stage is moved toward and away from said base member, said front surface of said first stage defining a vertical groove having a dovetail configuration;

a second stage having a shape substantially conforming to said dovetail configuration of said vertical groove of said front surface of said first stage and slidably fitting therewithin;

a third stage having a rear member, a front member and a spring mounting said front and rear members to one another and to said second stage and biasing said front member to said rear member, each of said rear and front members defining mateable radial splines, said front member rotatable in relation to said rear member by extension of said spring upon pulling said front member away from said rear member and rotating said front member and by retraction of said spring upon allowing said front member to fall back into mateable relation with said rear member, said front member attached to the retaining member and defining a groove for receiving an arch wire; and a plurality of adjustment screws, each of four of said adjustment screws threaded into and extending between said first stage and base member at one of said four corners of said first stage and base member for moving said first stage toward and away from said base member upon selected turning of each of said adjustment screws relative to said first stage and base member.

15. An adjustable orthodontic bracket assembly, comprising:

(a) a plurality of brackets each attachable to a front face of a tooth such that said bracket is positionable in series relation to one or more other of said brackets, each of said brackets including (i) a base member having opposite front and back surfaces, said back surface being attachable to the front face of the tooth, (ii) an upper horizontal post fixedly attached to said front surface of said base member and extending outwardly in substantially perpendicular relation thereto, (iii) a lower horizontal post fixedly attached to said front surface of said base member below and extending in substantially parallel relation to said upper horizontal post and outwardly in substantially perpendicular relation to said base member, (iv) a middle vertical post having opposite upper and lower ends, (v) a lower coupler movably mounted to said lower horizontal post such that said lower coupler is movable along said lower horizontal post toward and away from said base member, said lower coupler being pivotally connected to said lower end of said middle vertical post, (vi) an upper coupler movably mounted to said upper horizontal post such that said upper coupler is movable along said upper horizontal post toward and away from said base member, said upper coupler being pivotally connected to said upper end of said middle vertical post, and (vii) a retaining nut defining a groove for receiving an arch wire and being mounted to said middle vertical post to undergo movement between said upper and lower ends of said middle vertical post; and (b) an arch wire extending between said brackets in said series relation to one another and retained within said grooves of said retaining nuts of said brackets, said arch wire being biased to assume an original neutral configuration but being temporarily deformable from said original neutral configuration for accommodating adjustment of said brackets without said arch wire being removed therefrom.

16. The assembly of claim 15 wherein each of said bracket without replacement of any parts thereof is continuously adjustable in at least three orthogonal planes of motion.

17. The assembly of claim 16 wherein adjustment of each of said brackets in one of said at least three orthogonal planes of motion can be accomplished without affecting adjustment of said bracket in any of the other of said at least three planes of motion.

18. The assembly of claim 15 wherein each of said brackets is capable of adjustment in at least three of vertical, lateral and mesio/distal translational planes of motion and tip, torque and circular rotational planes of motion.

19. The assembly of claim 15 wherein said middle vertical post of each of said brackets has a length and a pair of spring-loaded end caps, each said spring-loaded end cap being mounted to one of said upper and lower ends thereof and allowing for variation of said length of said middle vertical post.

20. The assembly of claim 15 wherein said arch wire is made of a material which biases said arch wire to assume an original neutral configuration but allows said arch wire to be temporarily deformed by adjustment of said brackets for causing said deformed arch wire to apply corrective forces on said brackets as said arch wire returns to said original neutral configuration such that over time said arch wire causes the teeth to which said brackets are attached to move to desired corrected positions.

21. An adjustable orthodontic bracket assembly, comprising:

(a) a plurality of brackets each attachable to a front face of a tooth such that said bracket is positionable in series relation to one or more other of said brackets, each of said brackets including (i) a base member having opposite front and back surfaces, said back surface being attachable to the front face of the tooth, (ii) a pair of upper horizontal posts fixedly attached to said front surface of said base member and extending outwardly in substantially perpendicular relation thereto, (iii) a pair of lower horizontal posts fixedly attached to said front surface of said base member below and extending in substantially parallel relation to said upper horizontal posts and outwardly in substantially perpendicular relation to said base member, (iv) a pair of middle vertical posts each having opposite upper and lower ends, (v) a pair of lower couplers each movably mounted to one of said lower horizontal posts such that said lower coupler is movable along said lower horizontal post toward and away from said base member, each of said lower couplers being pivotally connected to said lower end of one of said middle vertical posts, (vi) a pair of upper couplers each movably mounted to one of said upper horizontal posts such that said upper coupler is movable along said upper horizontal post toward and away from said base member, each of said upper couplers being pivotally connected to said upper end of one of said middle vertical posts, and (vii) a pair of retaining nuts each defining a groove for receiving an arch wire and being mounted to one of said middle vertical posts for undergoing movement between said upper and lower ends of said one middle vertical post; and (b) an arch wire extending between said brackets in said series relation to one another and retained within said grooves of said retaining nuts of said brackets, said arch wire being biased to assume an original neutral configuration but being temporarily deformable from said original neutral configuration for accommodating adjustment of said brackets without said arch wire being removed therefrom.

22. The assembly of claim 21 wherein each of said bracket without replacement of any parts thereof is continuously adjustable in at least three orthogonal planes of motion.

23. The assembly of claim 22 wherein adjustment of each of said brackets in one of said at least three orthogonal planes of motion can be accomplished without affecting adjustment of said bracket in any of the other of said at least three planes of motion.

24. The assembly of claim 21 wherein each of said brackets is capable of adjustment in at least three of vertical, lateral and mesio/distal translational planes of motion and tip, torque and circular rotational planes of motion.

25. The assembly of claim 21 wherein each of said middle vertical posts of each of said brackets has a length and a pair of spring-loaded end caps, each of said spring-loaded end cap being mounted to one of said upper and lower ends thereof and allowing for variation of said length of said middle vertical post.

26. The assembly of claim 21 wherein said arch wire is made of a material which biases said arch wire to assume an original neutral configuration but allows said arch wire to be temporarily deformed by adjustment of said brackets for causing said deformed arch wire to apply corrective forces on said brackets as said arch wire returns to said original neutral configuration such that over time said arch wire causes the teeth to which said brackets are attached to move to desired corrected positions.

27. An adjustable orthodontic bracket assembly, comprising:

(a) a plurality of brackets each mountable to a front face of a tooth such that said bracket is positionable in series relation to one or more other said brackets, each of said brackets being in the form of a flexure element comprised of a resiliently deformable material and including (i) a base member having opposite front and back surfaces, said back surface being attachable to the front face of the tooth, (ii) a rear member having opposite upper and lower ends, one of said upper and lower ends having a rearward connection with said base member that spaces said rear member forwardly of said base member and defines a rear slot therebetween adjustable in cross-sectional size as said rear member is flexed via said rearward connection toward and away from said base member, (iii) a front member having opposite upper and lower ends, the other of said upper and lower ends of said rear member having a forward connection with a corresponding one of said upper and lower ends of said front member that spaces said front member forwardly of said rear member and defines a front slot therebetween adjustable in cross-sectional size as said front member is flexed via said forward connection toward and away from said rear member, (iv) a pair of adjustment screws, a first of said adjustment screws being threaded into and extending between said rear and base members for flexing said rear member toward and away from said base member upon selected turning of said first adjustment screw relative to said rear and base members, a second of said adjustment screws being threaded into and extending between said front and rear members for flexing said front member toward and away from said rear member upon selected turning of said second adjustment screw relative to front and rear members, (v) a vertical post having opposite upper and lower ends and extending between and mounted at said upper and lower ends thereof to said upper and lower ends of said front member, and (vi) a retaining nut defining a groove for receiving an arch wire and being mounted to said vertical post for undergoing movement between said upper and lower ends of said vertical post; and (b) an arch wire extending between said brackets in said series relation to one another and retained within said grooves of said retaining nuts of said brackets, said arch wire being biased to assume an original neutral configuration but being temporarily deformable from said original neutral configuration for accommodating adjustment of said brackets without said arch wire being removed therefrom.

28. The assembly of claim 27 wherein each of said brackets without replacement of any parts thereof is continuously adjustable in at least three orthogonal planes of motion.

29. The assembly of claim 28 wherein adjustment of each of said brackets in one of said at least three planes of motion can be accomplished without affecting adjustment of said bracket in any of the other of said at least three planes of motion.

30. The assembly of claim 27 wherein each of said brackets is capable of adjustment in at least three of vertical, lateral and mesio/distal translational planes of motion and tip, torque and circular rotational planes of motion.

31. The assembly of claim 27 wherein said arch wire is made of a material which biases said arch wire to assume an original neutral configuration but allows said arch wire to be temporarily deformed by adjustment of said brackets for causing said deformed arch wire to apply corrective forces on said brackets as said arch wire returns to said original neutral configuration such that over time said arch wire causes the teeth to which said brackets are attached to move to desired corrected positions.

32. An adjustable orthodontic bracket assembly, comprising:
   (a) a plurality of brackets each attachable to a front face of a tooth such that said bracket is positionable in series relation to one or more other of said brackets, each of said brackets being in the form of a flexure element comprised of a resiliently deformable material and including
      (i) a base member having opposite front and back surfaces, said back surface being attachable to the front face of the tooth,
      (ii) a pair of spaced apart rear members each having opposite upper and lower ends, one of said upper and lower ends of each of said rear members having a rearward connection with said base member that spaces said rear member forwardly of said base member and defines a rear slot therebetween adjustable in cross-sectional size as said rear member are flexed via said rearward connection toward and away from said base member,
      (iii) a pair of spaced apart front members each having opposite upper and lower ends, the other of said upper and lower ends of each of said rear members having a forward connection with a corresponding one of said upper and lower ends of one of said front members that spaces said front member forwardly of said respective rear member and defines a front slot therebetween adjustable in cross-sectional size as said front member is flexed via said forward connection toward and away from said rear member,
      (iv) a plurality of adjustment screws, a first pair of said adjustment screws threaded into and extending between said rear and base members for flexing said rear members toward and away from said base members upon selected turning of said adjustment screws of said first pair relative to said rear and base members, a second pair of said adjustment screws threaded into and extending between said front and rear members for flexing said front members toward and away from said rear members upon selected turning of said adjustment screws of said second pair relative to said front and rear members,
      (v) a pair of vertical posts each having opposite upper and lower ends and mounted at said upper and lower ends thereof to said upper and lower ends of one of said front members, and
      (vi) a pair of retaining nuts each defining a groove for receiving a common arch wire and being mounted to one of said vertical posts for undergoing movement between said upper and lower ends of said one of said front members; and
   (b) an arch wire extending between said brackets in said series relation to one another and retained within said grooves of said retaining nuts of said brackets, said arch wire being biased to assume an original neutral configuration but being temporarily deformable from said original neutral configuration for accommodating adjustment of said brackets without said arch wire being removed therefrom.

33. The assembly of claim 32 wherein each of said brackets without replacement of any parts thereof is continuously adjustable in at least three orthogonal planes of motion.

34. The assembly of claim 33 wherein adjustment of each of said brackets in one of said at least three orthogonal planes of motion can be accomplished without affecting adjustment of said bracket in any of the other of said at least three planes of motion.

35. The assembly of claim 32 wherein each of said brackets is capable of adjustment in at least three of vertical, lateral and mesio/distal translational planes of motion and tip, torque and circular rotational planes of motion.

36. The assembly of claim 32 wherein said arch wire is made of a material which biases said arch wire to assume an original neutral configuration but allows said arch wire to be temporarily deformed by adjustment of said brackets for causing said deformed arch wire to apply corrective forces on said brackets as said arch wire returns to said original neutral configuration such that over time said arch wire causes the teeth to which said brackets are attached to move to desired corrected positions.

37. An adjustable orthodontic bracket assembly, comprising:
   (a) a plurality of brackets each attachable to a front face of a tooth such that said bracket is positionable in series relation to one or more other of said brackets, each of said brackets being in the form of an adjustable arrangement of multiple stages and including
      (i) a base member having opposite front and back surfaces and four corners, said back surface being attachable to the front face of the tooth,
      (ii) a first stage having opposite front and back surfaces and four corners aligned with said four corners of said base member, said first stage and said base member defining a gap therebetween adjustable in cross-sectional size as said first stage is moved toward and away from said base member, said front surface of said first stage defining a vertical groove having a dovetail configuration,
      (iii) a second stage having a shape substantially conforming to said dovetail configuration of said vertical groove of said front surface of said first stage and slidably fitting therewithin,
      (iv) a third stage defining a groove for receiving an arch wire and being rotatably mounted to said second stage,
      (v) a plurality of adjustment screws, each of three of said adjustment screws threaded into and extending between said first stage and base member at one of said four corners of said first stage and base member for moving said first stage toward and away from said base member upon selected turning of each of said three adjustment screws relative to said first stage and base member, a pair of said adjustment screws spaced apart from one another and being secured through said third stage and threaded into said second stage for adjusting the rotational position of said third stage relative to said second stage upon untightening and retightening of said pair of adjustment screws, and
      (vi) spring means extending between and mounted to said first stage and base member at a fourth of said four corners of said first stage and base member for biasing said first stage toward said base member; and (b) an arch wire extending between said brackets in said series relation to one another and retained within said grooves of said retaining nuts of said brackets, said arch wire being biased to assume an original neutral configuration but being temporarily deformable from said original neutral configuration for accommodating adjustment of said brackets without said arch wire being removed therefrom.

38. The assembly of claim 37 wherein each of said brackets without replacement of any parts thereof is continuously adjustable in at least three orthogonal planes of motion.

39. The assembly of claim 38 wherein adjustment of each of said brackets in one of said at least three orthogonal planes of motion can be accomplished without affecting adjustment of said bracket in any of the other of said at least three planes of motion.

40. The assembly of claim 37 wherein each of said brackets is capable of adjustment in at least three of vertical, lateral and mesio/distal translational planes of motion and tip, torque and circular rotational planes of motion.

41. The assembly of claim 37 wherein said arch wire is made of a material which biases said arch wire to assume an original neutral configuration but allows said arch wire to be temporarily deformed by adjustment of said brackets for causing said deformed arch wire to apply corrective forces on said brackets as said arch wire returns to said original neutral configuration such that over time said arch wire causes the teeth to which said brackets are attached to move to desired corrected positions.

42. The assembly of claim 37 wherein said third stage of each of said brackets defines a pair of spaced apart and circumferentially directed slots receiving said adjustment screws therethrough such that loosening of said adjustment screws allows for rotation of said third stage and tightening of said adjustment screws secures said third stage in place relative to said first and second stages.

43. An adjustable orthodontic bracket assembly, comprising:
    (a) a plurality of brackets each attachable to a front face of a tooth such that said bracket is positionable in series relation to one or more other of said brackets, each of said brackets being in the form of an arrangement of multiple stages and including
        (i) a base member having opposite front and back surfaces and four corners, said back surface being attachable to the front face of the tooth,
        (ii) a first stage having opposite front and back surfaces and four corners aligned with said four corners of said base member, said first stage and said base member defining a gap therebetween adjustable in cross-sectional size as said first stage is moved toward and away from said base member, said front surface of said first stage defining a vertical groove having a dovetail configuration,
        (iii) a second stage having a shape substantially conforming to said dovetail configuration of said vertical groove of said front surface of said first stage and slidably fitting therewithin,
        (iv) a third stage having a rear member, a front member and a spring mounting said front and rear members to one another and to said second stage and biasing said front member to said rear member, each of said rear and front members defining mateable radial splines such that said front member may be rotated in relation to said rear member by extension of said spring upon pulling said front member away from said rear member and rotating said front member and by retraction of said spring upon allowing said front member to fall back into mateable relation with said rear member, said front member defining a groove for receiving an arch wire, and
        (v) a plurality of adjustment screws, each of four of said adjustment screws threaded into and extending between said first stage and base member at one of said four corners of said first stage and base member for moving said first stage toward and away from said base member upon selected turning of each of said adjustment screws relative to said first stage and base member; and
    (b) an arch wire extending between said brackets in said series relation to one another and retained within said grooves of said retaining nuts of said brackets, said arch wire being biased to assume an original neutral configuration but being temporarily deformable from said original neutral configuration for accommodating adjustment of said brackets without said arch wire being removed therefrom.

44. The assembly of claim 43 wherein each of said brackets without replacement of any parts thereof is continuously adjustable in at least three orthogonal planes of motion.

45. The assembly of claim 44 wherein adjustment of each of said brackets in one of said at least three orthogonal planes of motion can be accomplished without affecting adjustment of said bracket in any of the other of said at least three planes of motion.

46. The assembly of claim 43 wherein each of said brackets is capable of adjustment in at least three of vertical, lateral and mesio/distal translational planes of motion and tip, torque and circular rotational planes of motion.

47. The assembly of claim 43 wherein said arch wire is made of a material which biases said arch wire to assume an original neutral configuration but allows said arch wire to be temporarily deformed by adjustment of said brackets for causing said deformed arch wire to apply corrective forces on said brackets as said arch wire returns to said original neutral configuration such that over time said arch wire causes the teeth to which said brackets are attached to move to desired corrected positions.

* * * * *